US008313943B2

(12) United States Patent
Campbell

(10) Patent No.: US 8,313,943 B2
(45) Date of Patent: Nov. 20, 2012

(54) GENETICALLY MODIFIED HUMAN NATURAL KILLER CELL LINES

(75) Inventor: Kerry S. Campbell, Wyncote, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 285 days.

(21) Appl. No.: 12/564,283

(22) Filed: Sep. 22, 2009

(65) Prior Publication Data

US 2010/0086996 A1    Apr. 8, 2010

Related U.S. Application Data

(63) Continuation of application No. 11/178,258, filed on Jul. 8, 2005, now Pat. No. 7,618,817.

(60) Provisional application No. 60/586,581, filed on Jul. 10, 2004.

(51) Int. Cl.
 *C12N 5/00* (2006.01)
 *C12N 5/08* (2006.01)
 *C07K 1/00* (2006.01)
(52) U.S. Cl. ...... 435/325; 435/366; 435/372; 435/372.2
(58) Field of Classification Search .................. None
See application file for complete search history.

(56) References Cited

U.S. PATENT DOCUMENTS

| 3,773,919 | A |   | 11/1973 | Borwell et al. |
| 4,676,980 | A |   | 6/1987  | Segal et al. |
| 4,816,567 | A |   | 3/1989  | Cabilly et al. |
| 5,625,126 | A |   | 4/1997  | Lonberg et al. |
| 5,633,425 | A |   | 5/1997  | Lonberg et al. |
| 5,661,016 | A |   | 8/1997  | Lonberg et al. |
| 5,767,077 | A |   | 6/1998  | Peltz et al. |
| 5,830,725 | A |   | 11/1998 | Nolan et al. |
| 5,976,831 | A |   | 11/1999 | Peltz et al. |
| 7,038,031 | B1| * | 5/2006  | Ravetch et al. ............. 536/23.5 |
| 7,618,817 | B2| * | 11/2009 | Campbell ..................... 435/325 |

FOREIGN PATENT DOCUMENTS

| EP | 0758394  | 2/1997  |
| WO | 9100360  | 1/1991  |
| WO | 9220373  | 11/1992 |
| WO | 9733551  | 9/1997  |
| WO | 98/49268 | 11/1998 |

OTHER PUBLICATIONS

Ravetch, Jeffrey V. et al., Alternative Membrane Forms of FcγRIII(CD16) on Human Natural Killer Cells and Neutrophils: Cell Type-Specific Expression of Two Genes that Differ in Single Nucleotide Substitutions, J. Exp. Med. vol. 170: 481-97, Aug. 1989.
Wu, Jianming et al., A Novel Polymorphism of FcγRIIIa(CD16) Alters Receptor Function and Predisposes to Autoimmune Disease, J. Clin. Invest., vol. 100(5): 1059-70, Sep. 1997.
Marks, J.D. et al., By-Passing Immunization: Building High Affinity Human Antibodies by Chain Shuffling, Bio Technology vol. 10, Jul. 1992, p. 779-83.
Nagashima, S. et al., Stable Transduction of the Inerleukin-2 Gene into Human Natural Killer Cell Lines and Their Phenotypic and Functional Characterization In Vitro and In Vivo, Blood, vol. 91(10): 3850-61.
Reisfeld, R.A. et al., Monoclonal Antibodies and Cancer Therapy, UCLA Symposia on Molecular and Cellular Biology, Journal of Cellular Biochemistry, Abstracts: 141st Annual Meeting, Jan. 12-Feb. 6, 1985.
Longberg, N. et al., Human Antibodies from Trangenic Mice, Inter. Rev. Immunol., vol. 13: 65-93, 1995.
Uherek, C. et al., Chimeric Antigen Receptors for the Retargeting of Cytotoxic Effector Cells, Journal of Hematotherapy & Stem Cell Research, 10: 523-34, 2001.
Cooper, M.A. et al., The Biology of Human Natural Killer-Cell Subsets, TRENDS in Immuniology, vol. 22 (11): 633-40, Nov. 2001.
Crew, M.D. et al., An HLA-E Single Chain Trimer Inhibits Human NK Cell Reactivity Towards Porcine Cells, Molecular Immunology 42: 1205-14, 2005.
Drexler, HG et al., Malignant Hematopoietic Cell Lines: In Vitro Models for the Study of Natural Killer Cell Leukemia-Lymphoma, Leukemia, vol. 14: 777-82, 2000.
Gross, C. et al., Heat Shock Protein 70-Reactivity is Associated with Increased Cell Surface Density of CD94/CD56 on Primary Natural Killer Cells, Cell Stress & Chaperones 8 (4): 348-60, 2003.
Robertson, M.J. et al., Characterization of a Cell Line, NKL, Derived from an Aggressive Human Natural Killer Cell Leukemia, Experimental Hematology 24: 406-15, 1996.
Bodine, D.M. et al., Survival and Retrovirus Infection of Murine Hematopoietic Stem Cells in Vitro . . . , Exp. Hematology 19: 206-12, 1991.
Toureav, A. et al., Plant Male Germ Line Transformation, The Plant Journal 4: 949-56, 1997.
Chen, C.A. et al., Calcium Phosphate-Mediated Gene Transfer: A Highly Efficient Transfection System for Stably Transforming Cells with Plasmid DNA, BioTech 6 (7): 632-8, 1988. Komatsu, F. et al., Relation of Natural Killer Cell Line NK-92-Mediated Cytolysis with the Surface Markers of Major Histocompatibility . . . , Oncol. REs. 10: 483-89, 1998.
Suresh, M.R. et al., Bispecific Monoclonal Antibodies from Hybrid Hybridomas, Methods in Enzymology 121: 210-28, 1986.
Kaufman, R., Vectors used for Expression in Mammalian Cells, Methods in Enzymology 185: 487-511, 1990.
Graham, F.L. et al., A New Technique for the Assay of Infectivity of Human Adenovirus 5 DNA, Virology 52: 456-67, 1973.
Potter, H., Electroporation in Biology: Methods, Applications and Instrumentation, Analytical Biochemistry 174: 361-73, 1988.
Traunecker, A. et al., Myeloma Based Expression System for Production of Large Mammalian Proteins, Tibtech 9: 109-13, Apr. 1991.
Koehne, G et al., Redirecting NK-Cell Cytoloytic Activity to Solid Tumors Using Chimeric scFv Receptor Gene-Modified Adoptive Immuno., Proc. ASCO 22: 703, 2003 (abstract).

(Continued)

*Primary Examiner* — Chun Dahle
(74) *Attorney, Agent, or Firm* — Alicia M. Passerin, Esq.; Pietragallo Gordon Alfano Bosick & Raspanti, LLP

(57) ABSTRACT

The invention provides a natural killer cell, NK-92, modified to express an Fc receptor on the surface of the cell, such as CD16 (FcγRIII-A), or other Fcγ or Fc receptors. The modified NK-92 cell can be further modified to concurrently express an associated accessory signaling protein, such as FcεRI-γ, TCR-ζ, or to concurrently express interleukin-2 (IL-2) or other cytokines. Additional methods are disclosed for various assays, assessments, and therapeutic treatments with the modified NK-92 cells.

2 Claims, 5 Drawing Sheets

OTHER PUBLICATIONS

Deaglio, S. et al., Human CD38 and CD16 are Functionally Dependent and Physically Associated in Natural Killer Cells, Blood 99 (7): 2490-98, Apr. 1, 2002.
Mandelboim, O. et al., Human CD16 as a Lysis Receptor Mediating Direct Natural Killer Cell Cytotoxicity, Proc. Natl. Acad. Sci. 96: 5640-44, May 1999.
Zhang, J. et al., Characterization of Interleukin-15 Gene-Modified Human Natural Killer Cells: Implications for Adoptive Cellular Immu., Haematologica 89 (3): 338-47, Mar. 2004.
Zhang, J. et al., Characterization of Stem Cell Factor Gene-Modified Human Natural Killer Cell Line . . . , Oncology Reports 11: 109-1106, 2004.
Ernst, L. et al., Allelic Polymorphisms in the FcγRIIC Gene can Influence its Function on Normal Human Natural Killer Cells, J. Mol. Med. 80: 248-57, 2002.
Altschul, S. et al., Gapped BLAST and PSI-BLAST: A New Generation of Protein Database Search Programs, Nuc. Acids Res. 25 (17): 3389-402, 1997.
Austin, C. et al., Cellular Migration Patterns in the Developing Mouse Cerebral Cortex, Development 110: 713-32, 1990.
Boerner, P. et al., Production of Antigen-Specific Human Monoclonal Antibodies from In Vitro-Primed Human Splenocytes, J. Immunol. 147 (1): 86-95, 1991 (abstract).
Brennan, M. et al., Preparation of Bispecific Antibodies by Chemical Recombination of Monoclonal Immunoglobuln G1 Fragments, Science 229 (4708): 81-3, Jul. 5, 1985 (abstract).
Campbell, K. et al., NKp44 Triggers NK Cell Activation through DAP12 Association . . . , J. Immunol. 172: 900-6, 2004.
Capecchi, M., High Efficiency Transformation by Direct Microinjection of DNA into Cultured Mammalian Cells, Cell vol. 22 (2): 479-88, Nov. 1980 (abstract).
Carter, P., Site-Directed Mutagenesis, Biochem. J. 237: 1-7, 1986.
Cepko, C. et al., Construction and Applications of a Highly Transmissible Murine Retrovirus Shuttle Vector, Cell vol. 37 (3): 1053-62, Jul. 1984 (abstract).
Chaney, W. et al., High-Fequency Transfecton of CHO Cells Using Polybrene, Somatic Cell and Mol Gene, vol. 12 (3): 237-44, May 1986 (abstract).
Clark, J. et al., Induction of Multiple Anti-c-erbB-2 Specificities Accompanies a Classical Idotypic . . . , Can Immuno vol. 44(5): 265-322, Jul. 1997 (abstract).
Elroy-Stein, O. et al., Cytoplasmic Expression System Based on Constitutive Synthesis of Bacteriophage T7 RNA Polymerase . . . , Proc. Natl. Acad. Sci. 8: 6743-47, 1990 (abstract).
Escudero, J. et al., Transfer and Integration of T-DNA Without Cell Injury in the Host Plant, The Plant Cell, vol. 9 (12): 2135-42, 1997 (abstract).
Vitale, M. et al., NKp44, a Novel Triggering Surface Molecule Specifically Expressed by Activated Natural Killer Cells . . . , J. Exp. Med. 187 (12): 2065-72, 1998.
Weiner, LM et al. Phase I Trial 2B1, A Bispecific Monoclonal Antibody Targeting c-erbB-2 and Fc Gamma RIII, Cancer Res 55 (20): 4586-93, 1995 (abstract).
Winer, LM et al., Clinical Development of 2B1, A Bispecific Murine Monoclonal Antibody Targeting c-erbB-2 and Fc Gamma RIII, J Hematother 4 (5): 453-56, 1995 (abstract).
Weiner, LM et al., Binding and Cytotoxicity Characteristics of the Bispecific Murine Monoclonal Antibody 2B1, J. Immunol. 151 (5):2877-86, 1993 (abstract).
Wells, JA et al., Cassette Mutagenesis: An Efficient Method for Generation of Multiple Mutations at Defined Sites, Gene 34 (2-3): 315-23, 1985 (abstract).
Wigler, M. et al., Biochemical Transfer of Single-Copy Eucaryotic Genes Using Total Cellular DNA as Donor, Cell 14 (3): 725-31, 1978 (abstract).
Wilmut, I. et al., Viable Offspring Derived from Fetal and Adult Mammalian Cells, Nature 385 (6619): 810-13, 1997 (abstract).
Wong, T. et al., Electric Field Mediated Gene Transfer, Biochem & Biophys Res Comm 107 (2): 584-87, 1982 (abstract).
Wyborski, D. et al., Other Transgenic Mutation Assays: Parameters Affectng the Use of the LAC Repressor System . . . , Env & Mole Mut 28 (4): 447-58, 1998 (abstract).
Wyborski, D. et al., Analysis of Inducers of the E.coli LAC Repressor System Mammalian Cells and Whole Animals, Nuc. Acids Res 19 (17): 4647-59, 1991 (abstract).
Yan, Y. et al., Antileukemia Activity of a Natural Killer Cell Line Against Human Leukemias, Clin. Can. Res. 4: 2859-68, 1998.
Yusa, S. et al., SRC Homology Region2-Containing Protein Tyrosine Phosphatase-2 (SHP-2) Can Play a Direct Role . . . , J. Immunol. 170: 4539-47, 2003.
Yusa, S. et al., SHP-1- and phosphotyrosine-Independent Inhibitory Signaling by a Killer Cell Ig-like Receptor Cytoplasmic Domain . . . , J. Immunol. 168: 5047-57, 2002.
Yusa, S. et al., KIR2DL5 can Inihibit Human NK Cell Activation Via Recruitment of SRC Homology Region 2-Contanining Protein . . . , J. Immunol. 172: 7385-92, 2004.
Zoller, MJ et al., Oligonucleotide-Directed Mutagenesis: A Simple Method Using Two Oligonucleotide Primers . . . , Methods Enzymol 154: 329-50, 1987 (abstract).
Fekete, DM et al., Retroviral Infection Coupled with Tissue Transplantation Limits Gene Transfer in the Chicken Embryo, Proc. Natl. Acad. Sci. 90: 2350-54, 1993 (abstract).
Feigner, P. et al., Lipofection: A Highly Efficient, Lipid-Mediated DNA-Transfection Procedure, Proc. Natl. Acad. Sci. vol. 84 (21): 7413-17, Nov. 1987 (abstract).
Fieck, A. et al., Modifications of the E. coli Lac Repressor for Expression in Eukaryotic Cells: Effects of Nuclear Signal . . . , Nuc Acids Res 20 (7): 1785-91, 1992.
Fishwild, D.M. et al., High-Avidity Human IgGk Monoclonal Antibodies from a Novel Starin of Minilocus Transgenic Mice, Nature Biotechnology 14: 845-57, 1996 (abstract).
Fleit, H.B. et al., Human Neutrophil Fc, Receptor Distribution and Structure, Proc. Natl. Acad. Sci. 79: 3275-79, 1982.
Fujita, T. et al., Regulation of Human Interleukin-2 Gene: Functional DNA Sequences in the 5' Flanking Region for the Gene . . . , Cell 46 (3): 401-7, 1986 (abstract).
Gerstmayer, B. et al., Stable Expression of the Ecotropic Retrovirus Receptor in Amphotropic Packaging Cells . . . , J. Viro. Meth. 81 (1-2): 71-5, 1999 (abstract).
Gong, L. et al., Characterization of a Human Cell Line (NK-92) with Phenotypical and Functional Characteristics of Activated Natural Killer Cells, Leukemia 8 (4): 652-58, 1994.
Gruber, M. et al., Efficient Tumor Cell Lysis Mediated by a Bispecific Single Chain Antibody Expressed in Escherichia coli, J. Immunol. 152 (11): 5368-74, 1994 (abstract).
Holliger, P. et al., Diabodies: Small Bivalent and Bispecific Antibody Fragments, Proc. Natl. Acad. Sol. 90: 6444-84, 1993.
Hoogenboom, H. et al., Multi-Subunit Proteins on the Surface of Filamentous Phage: Methodologies for Displaying . . . , Nuc. Acids Res. 19 (15): 4133-37, 1991 (abstract).
Huang, J. et al., The Emotif Database, Nuc. Acids Res. 202-04, 2001.
Ishiura, M. et al., Phage Particle-Mediated Gene Transfer to Cultured Mammalian Cells, Mol. Cell Bio. 2 (6): 607-16, 1982 (abstract).
Jones, P. et al., Replacing the Complementarity-Determining Regions in a Human Antibody with those from a Mouse, Nature 321: 522-25, 1986 (abstract).
Kawai, S. et al., New Procedure for DNA Transfection with Polycation and Dimetyl Sulfoxide, Mol Cell Biol 4 (6): 172-74, 1984 (abstract).
Kikuchi-Maki, A. et al., KIR2DL4 is an IL-2 Regulated NK Cell Receptor that Exhibits Limited Expression in Humans . . . , J. Immunol 171: 3415-25, 2003.
Kinsella, TM et al., Episomal Vectors Rapidly and Stably Produce High-Titer Recombinant Retrovirus, Hum Gene Ther 7 (12): 1405-13, 1996 (abstract).
Koene, H. et al., RcaRIIIa-158V/F Polymorphism Influences the Binding of IgG by Natural Killer Cell . . . , Blood 90 (3): 1109-14, 1997.
Kostelny, SA et al., Formation of a Bispecific Antibody by the Use of Leucine Zippers, J. Immunol. 148 (5): 1547-53, 1992 (abstract).
Lam, K., Mini-review: Application of Combinatorial Library Methods in Cancer Research and Drug Discovery, Anti-Cancer Drug Design 12 (3): 145-67, 1997 (abstract).
Lemischka, I. et al., Developmental Potential and Dynamic Behavior of Hematopietic Stem Cells, Cell 45 (6): 917-27, 1986 (abstract).

Linder, M. et al., Pharmacogenetics: A Laboratory Tool for Optimizing Therapeutic Efficiency, Clin. Chem. 43: 254-66, 1997.

Lonberg, N. et al., Antigen-Specific Human Antibodies from Mice Comprising Four Distinct Genetic Modifications, Nature 368: 856-59, 1994 (abstract).

Lopata, M. et al., High Level Transient Expression of a Chloramphenicol Acetyl Transferase Gene . . . , Nuc. Acids Res. 12 (14): 5707-17, 1984 (abstract).

Maki, G. et al., Factors Regulating the Cytotoxic Activity of the Human Natural Killer Cell Line, NK-92, J Hematother Stem Cell Res 10 (3): 369-83, 2001 (abstract).

Marasco, W. et al., Design, Intracellular Expression, and Activity of a Human Anti-Human Immunodeficiency Virus Type . . . , Proc. Natl. Acad. Sci. 90: 7889-93, 1993.

Marks, J. et al., By-Passing Immunization: Human Antibodies from V-Gene Libraries Displayed on Phage, J. Mol. Biol. 222 (3): 581-97, 1991 (abstract).

Miller, A. et al., Redesign of Retrovirus Packaging Cell Lines to Avoid Recombination Leading to Helper Virus Production, Mol. & Cell. Biol. 6 (8): 2895-902, 1986.

Milstein, C. et al., Hybrid Hybridomas and Their Use in Immunohistochemistry, Nature 305: 537-40, 1983 (abstract).

Nagashima, S. et al., Stable Transduction of the Interleukin-2 Gene into Human Natural Killer Cell Lines and Their Phenotypic . . . , Blood 91 (10): 3850-61, 1998.

Neumann, E. et al., Gene Transfer into Mouse Lyoma Cells by Electroporation in High Electric Fields, EMBO J. 1 (7): 841-45, 1982 (abstract).

Pear, W. et al., Production of High-Titer Helper-Free Retroviruses by Transient Transfection, Proc. Natl. Acad. Sci. 90: 8392-96, 1993.

Pende, D. et al., Identification and Molecular Characterization of NKp30, a Novel Triggering Receptor . . . , J. Exp. Med. 190 (10): 1505-16, 1999.

Perussia, B. et al., Antibody 3G8, Specific for the Human Neutrophil Fc Receptor, Reacts with Natural Killer Cells, J. Immunol. 132 (3): 1410-15, 1984 (abstract).

Perssino, A. et al., Molecular Cloning of NKp46: A Novel Member of the Immunoglobulin Superfamily Involved in Triggering . . . , J. Exp. Med. 188 (5): 953-60, 1998.

Potter, H. et al., Enhancer-Dependent Expression of Human K Immunoglobulin Genes . . . , Proc. Natl. Acad. Sci. 81: 7161-65, 1984.

Presta, LG, Antibody Engineering, Curr Opin Biotechnol 3(4): 394-98, 1992 (abstract).

Rassoulzadegan, M. et al., High Frequency of Gene Transfer After Fusion Between Bacteria and Eukaryotic Cells, Nature 295: 257-59, 1982 (abstract).

Reid, G. et al., Differntial Killing of Pre-B Acute Lymphoblastic Leukemia Cells by Activated NK Cells and the NK-92 Cl Cell Line, Clin Exp Immunol 129: 265-71, 2002.

Riechmann, L. et al., Reshaping Human Antibodies for Therapy, Nature 332: 323-27, 1988 (abstract).

Rose, JK et al., A New Cationic Liposome Reagent Mediating Nearly Quantitative Transfection of Animal Cells, Biotechniques 10(4):520-25, 1991 (abstract).

Sandri-Goldin, R. et al., High-Frequency Transfer of Cloned Herpes Simplex Virus Type 1 Sequences to Mammalian Cells by Protoplast Fusion, Mol. & Cell. Bio. 1 (8).

Schaffner, W., Direct Transfer of Cloned Genes from Bacteria to Mammalian Cells, Proc. Natl. Acad. Sci. 77 (4): 2163-67, 1980.

Selden, R. et al., Human Growth Hormone as a Reporter Gene in Regularion Studies Employing Transient Gene Expression, Mol & Cell Biol 6 (9): 3173-79, 1986.

Shalaby, M. et al Development of Humanized Bispecific Antibodies Reactive with Cytotoxic Lymphocytes and Tumor Cells Overexpressing . . . , J. Exp. Med. 175:217-25, 1992.

Tam, Y. et al., Characterization of Genetically Altered, Interleukin 2-independent Natural Killer Cell Lines . . . , Hum Gene Ther 10 (8): 1359-73, 1999 (abstract).

Turner, D. et al., Lineage-Independent Determination of Cell Type in the Embryonic Mouse Retina, Neuron 4 (6): 833-45, 1990 (abstract).

Tutt, A. et al., Trispecific F(ab')3 Derivatives that Use Cooperative Signaling via the TCR/CD3 Complex . . . , J. Immunol. 147 (1): 60-9, 1991 (abstract).

Uherek, C. et al., Retargeting of Natural Killer-Cell Cytolytic Activity to ErbB2-expressing Cancer Cells . . . , Blood 100 (4): 1265-73, 2002.

Verhoeye, M. et al., Reshaping Human Antibodies: Grafting an Antilysozyme Activity, Science 239 (4847): 1534-36, 1988 (abstract).

UniProtKB/Swiss-Prot P08637 (FCG3A_Human), Low affinity immunoglobulin gamma Fc region receptor III-A, Oct. 13, 2009, Version 115, pp. 1-10.

* cited by examiner

SEQUENCE LISTING

```
<160> NUMBER OF SEQ ID NOS: 7

<210> SEQ ID NO 1
<211> LENGTH: 254
<212> TYPE: PRT
<213> ORGANISM: Homo sapiens

<400> SEQUENCE: 1

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125
```

```
His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
                195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 2
<211> LENGTH: 254
<212> TYPE: PRT
<213> ORGANISM: Homo sapiens

<400> SEQUENCE: 2

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Val Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
                195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 3
<211> LENGTH: 765
<212> TYPE: DNA
<213> ORGANISM: Homo sapiens

<400> SEQUENCE: 3

```
atgtggcagc tgctcctccc aactgctctg ctacttctag tttcagctgg catgcggact      60
gaagatctcc caaaggctgt ggtgttcctg gagcctcaat ggtacagggt gctcgagaag     120
gacagtgtga ctctgaagtg ccagggagcc tactccctg aggacaattc cacacagtgg      180
tttcacaatg agagcctcat ctcaagccag gcctcgagct acttcattga cgctgccaca     240
gtcgacgaca gtggagagta caggtgccag acaaacctct ccaccctcag tgacccggtg     300
cagctagaag tccatatcgg ctggctgttg ctccaggccc ctcggtgggt gttcaaggag     360
gaagacccta ttcacctgag gtgtcacagc tggaagaaca ctgctctgca taaggtcaca     420
tatttacaga atggcaaagg caggaagtat tttcatcata attctgactt ctacattcca     480
aaagccacac tcaaagacag cggctcctac ttctgcaggg ggcttttgg gagtaaaaat      540
gtgtcttcag agactgtgaa catcaccatc actcaaggtt tggcagtgtc aaccatctca     600
tcattctttc cacctgggta ccaagtctct ttctgcttgg tgatggtact cctttttgca     660
gtggacacag gactatattt ctctgtgaag acaaacattc gaagctcaac aagagactgg     720
aaggaccata atttaaatg gagaaaggac cctcaagaca aatga                      765
```

<210> SEQ ID NO 4
<211> LENGTH: 591
<212> TYPE: DNA
<213> ORGANISM: Homo sapiens

<400> SEQUENCE: 4

```
cagaacggcc gatctccagc ccaagatgat tccagcagtg gtcttgctct tactcctttt      60
ggttgaacaa gcagcggccc tgggagagcc tcagctctgc tatatcctgg atgccatcct     120
gtttctgtat ggaattgtcc tcaccctcct ctactgtcga ctgaagatcc aagtgcgaaa     180
ggcagctata accagctatg agaaatcaga tggtgtttac acgggcctga gcaccaggaa     240
ccaggagact tacgagactc tgaagcatga gaaaccacca cagtagcttt agaatagatg     300
cggtcatatt cttctttggc ttctggttct tccagccctc atggttggca tcacatatgc     360
ctgcatgcca ttaacaccag ctggccctac ccctataatg atcctgtgtc taaattaat      420
atacaccagt ggttcctcct ccctgttaaa gactaatgct cagatgctgt ttacggatat     480
ttatattcta gtctcactct cttgtcccac ccttcttctc ttccccattc ccaactccag     540
ctaaaatatg ggaagggaga acccccaata aaactgccat ggactggact c              591
```

<210> SEQ ID NO 5
<211> LENGTH: 86
<212> TYPE: PRT
<213> ORGANISM: Homo sapiens

<400> SEQUENCE: 5

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

```
Gln Val Arg Lys Ala Ala Ile Thr Ser Tyr Glu Lys Ser Asp Gly Val
    50                  55                  60
Tyr Thr Gly Leu Ser Thr Arg Asn Gln Glu Thr Tyr Glu Thr Leu Lys
65                  70                  75                  80
His Glu Lys Pro Pro Gln
                85

<210> SEQ ID NO 6
<211> LENGTH: 1472
<212> TYPE: DNA
<213> ORGANISM: Homo sapiens

<400> SEQUENCE: 6
cttttctcct aaccgtcccg gccaccgctg cctcagcctc tgcctcccag cctctttctg      60
agggaaagga caagatgaag tggaaggcgc ttttcaccgc ggccatcctg caggcacagt     120
tgccgattac agaggcacag agctttggcc tgctggatcc caaactctgc tacctgctgg     180
atggaatcct cttcatctat ggtgtcattc tcactgcctt gttcctgaga gtgaagttca     240
gcaggagcgc agagcccccc gcgtaccagc agggccagaa ccagctctat aacgagctca     300
atctaggacg aagagaggag tacgatgttt tggacaagac gtggccgg accctgaga       360 tgggggaaa gccgagaagg aagaaccctc aggaaggcct gtacaatgaa ctgcagaaag     420
ataagatggc ggaggcctac agtgagattg ggatgaaagg cgagcgccgg aggggcaagg     480
ggcacgatgg cctttaccag gtctcagta cagccaccaa ggacacctac gacgcccttc     540
acatgcaggc cctgcccct cgctaacagc aggggattt caccactcaa aggccagacc     600
tgcagacgcc cagattatga cacaggat gaagcattta acccggtt cactcttctc      660 agccactgaa gtattcccct ttatgtacag gatgctttgg ttatatttag ctccaaacct     720
tcacacacag actgttgtcc ctgcactctt aagggagtg tactcccagg cttacggcc      780 ctgccttggg ccctctggtt tgccggtggt gcaggtagac ctgtctcctg gcggttcctc     840
gttctccctg ggaggcgggc gcactgcctc tcacagctga gttgttgagt ctgttttgta     900
aagtccccag agaaagcgca gatgctagca catgccctaa tgtctgtatc actctgtgtc     960
tgagtggctt cactcctgct gtaaatttgg cttctgttgt caccttcacc tccttttcaag   1020 gtaactgtac tgggccatgt tgtgcctccc tggtgagagg gccgggcaga ggggcagatg    1080
gaaaggagcc taggccaggt gcaaccaggg agctgcaggg gcatgggaag gtgggcgggc    1140
aggggagggt cagccaggc ctgcgagggc agcgggagcc tccctgcctc aggcctctgt    1200
gccgcaccat tgaactgtac catgtgctac aggggccaga agatgaacag actgaccttg    1260
atgagctgtg cacaaagtgg cataaaaaac agtgtggtta cacagtgtga ataaagtgct    1320
gcggagcaag aggaggccgt tgattcactt cacgctttca gcgaatgaca aaatcatctt    1380
tgtgaaggcc tcgcaggaag acgcaacaca tgggacctat aactgcccag cggacagtgg    1440
caggacagga aaaacccgtc aatgtactag gg                                 1472

<210> SEQ ID NO 7
<211> LENGTH: 163
<212> TYPE: PRT
<213> ORGANISM: Homo sapiens

<400> SEQUENCE: 7

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30
```

-continued

```
Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Glu Pro Pro Ala Tyr
 50                  55                  60

Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Arg Gly Arg Asp Pro Glu Met
                 85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
            115                 120                 125

Gly Glu Arg Arg Arg Gly Lys Gly His Asp Gly Leu Tyr Gln Gly Leu
        130                 135                 140

Ser Thr Ala Thr Lys Asp Thr Tyr Asp Ala Leu His Met Gln Ala Leu
145                 150                 155                 160

Pro Pro Arg
```

GENETICALLY MODIFIED HUMAN NATURAL KILLER CELL LINES

CROSS-REFERENCE TO RELATED APPLICATION

This application is a continuation of U.S. patent application Ser. No. 11/178,258, filed Jul. 8, 2005, entitled "GENETICALLY MODIFIED HUMAN NATURAL KILLER CELL LINES," which claims priority to U.S. Provisional Patent Application No. 60/586,581, filed Jul. 10, 2004, entitled "A GENETICALLY MODIFIED HUMAN NATURAL KILLER (NK) CELL LINE," the entirety of which is herein incorporated by reference.

STATEMENT REGARDING FEDERALLY SPONSORED RESEARCH OR DEVELOPMENT

This invention was made in part with grants from the National Institutes of Health: NIH R01 CA083859 (NCI; 2000-2009), entitled "Negative signaling by killer cell Ig-like receptors" and NIH R01 CA100226 (NCI; 2004-2009), entitled "Mechanisms of NK cell activation by the KIR2DL4 receptor." The government may have certain rights in the invention.

INCORPORATION-BY-REFERENCE OF MATERIAL SUBMITTED ON A COMPACT DISC

N/A

FIELD OF THE INVENTION

This invention relates generally to certain natural killer (NK) cell lines that have been genetically engineered to express a cell surface receptor protein that participates in antibody-dependent cellular cytotoxicity responses. More specifically, the present invention relates to a natural killer cell line NK-92 which, in a first embodiment, has been modified to express an Fc cell surface receptor protein such as CD16, and in a second embodiment, has been modified to express both an Fc cell surface receptor protein such as CD16 and one or more of the associated accessory signaling proteins such as FcR-γ or TCR-ζ and/or a cytokine such as IL-2.

BACKGROUND

A number of antibodies, most notably Rituximab (MabThera®; Hoffmann-LaRoche, Ltd; Basel, Switzerland) and Herceptin® (Genentech, Inc.; South San Francisco, Calif.), have shown significant therapeutic value as highly selective and effective anti-tumor agents. Although these antibodies can bind to specific antigens on the tumor cells, their anti-tumor activity depends at least in part on the subsequent binding of natural killer (NK; a table of abbreviations is provided in Table Z, located after the Examples) cells to the Fc (constant) portion of the antibody with consequent destruction of the tumor cell via an antibody-dependent cellular cytotoxicity (ADCC) mechanism.

NK cells are a class of lymphocytes that typically comprise approximately 10% of the lymphocytes in a human. The primary function of NK cells is to provide an innate cellular immune response against tumor and infected (target) cells. Roles in the priming and regulation of humoral immune response, fetal development and the elimination of stressed or damaged normal cells have also been demonstrated and/or are considered to be likely. NK cells, which are characterized as having a CD3$^-$/CD56$^+$ phenotype, display a variety of activating and inhibitory cell surface receptors. The binding or ligation of an activating NK cell receptor to the corresponding ligand on a target cell triggers the NK cell to exert a cytotoxic effect directly against the target cell and to secrete a variety of cytokines that perform functions such as the stimulation and recruitment of other elements of the immune system to act against the target. Activated NK cells lyse target cells via the secretion of the enzymes perforin and granzyme, stimulation of apoptosis-initiating receptors and other less well characterized mechanisms.

NK cell inhibitory receptors predominantly engage with major histocompatibility complex class I ("MHC-I") proteins on the surface of a normal cell. When so engaged, these inhibitory receptors prevent NK cells from becoming activated. The MHC-I molecules define cells as "belonging" to a particular individual. As expression of these MHC-I molecules can prevent NK cell activation toward a target cell, it is thought that NK cells can be activated only by cells on which these "self" MHC-I molecules are missing or defective, such as is often the case for tumor or virus-infected cells. The NK cell phenotype and activation pattern are distinct from that exhibited by cytotoxic T-lymphocytes ("CTLs," CD3$^+$/CD56$^-$/CD8$^+$ phenotype) that are activated by target cells that display small foreign peptide fragments derived from viruses or tumor cells attached to the surface MHC-I molecules. Scientists have speculated that NK cells evolved as a response to tumor and infected cells that evade destruction by CTLs through suppression or disruption of the display of peptide-presenting MHC-I molecules.

NK cells have been evaluated as a therapeutic agent in the treatment of certain cancers. The NK cells used for this purpose are isolated from the peripheral blood lymphocyte ("PBL") fraction of blood from the subject, expanded in cell culture in order to obtain sufficient numbers of cells, and then re-infused into the subject. Although the results of this therapy have been promising, preparation of the autologous NK cells is expensive, labor intensive and time consuming. Furthermore, quality control of these cells is complicated by each preparation being subject specific. In particular, the quantity of NK cells that can be isolated from a subject can vary substantially, and these cells are often deficient in proliferative ability and/or cytotoxic activity. Another limitation on the use of NK cells as a therapeutic agent results from the presence of surface antigens on the cells that can evoke an immune rejection response when the cells are infused into a subject other than the one from which they were isolated. This necessitates careful MHC-I cross-matching between the donor and the recipient as well as the need to immuno-suppress the recipient.

The NK-like cell line NK-92 was discovered in the blood of a subject suffering from a non-Hodgkins lymphoma. NK-92 cells lack the major inhibitory receptors that are displayed by normal NK cells, but retain the majority of the activating receptors. Characterization of the NK-92 cell line (Gong et al., 1994; Yan et al., 1998) revealed that NK-92 cells are cytotoxic to a significantly broader spectrum of tumor and infected cell types than are NK cells, and further that they often exhibit higher levels of cytotoxicity toward these targets. NK-92 cells do not, however, attack normal cells nor do they elicit an immune rejection response. In addition, NK-92 cells can be readily and stably grown and maintained in continuous cell culture and, thus, can be prepared in large quantities under c-GMP compliant quality control. This combination of characteristics has resulted in NK-92 being entered into presently on-going clinical trials for the treatment of multiple types of cancers.

Although NK-92 cells retain almost all of the activating receptors and cytolytic pathways associated with NK cells, they do not express the CD16 receptor and, therefore, cannot lyse target cells via the ADCC mechanism. This means that despite their other benefits, NK-92 cells cannot potentiate the anti-tumor and anti-infection effects of endogenous or exogenous antibodies in the manner of NK cells. Other NK-like cell lines in addition to NK-92 are also known. Some of these other NI-like cell lines express CD16, but this expression is unstable; the cells are typically difficult to grow in cell culture; and few exhibit robust cytotoxic activity. For these reasons, only NK-92 of the currently known NK-like cell lines is a viable candidate as a therapeutic agent even though it lacks CD16 and, consequently, the ability to kill target cells via the ADCC mechanism.

Thus, it would be an advantage to restore CD16 expression and the ability to act via the ADCC mechanism to NK-92 cells, thus permitting those cells to be used in concert with antibodies for therapeutic and related purposes. However, NK cell lines have been found to be recalcitrant to gene transfer, a feature that has hampered the development of such cell lines for research or therapeutic purposes. For NK-92 cells, transformation efficiencies of only 5-15% and 10-20% have been achieved using particle-mediated gene transfer or retroviral transduction (Nagashima et al., 1998; Tam et al., 1999). NK-92 cell lines that stably expresses the CD16 cell surface receptor are currently unavailable.

SUMMARY

The various embodiments of the invention provide or utilize an NK-92 cell modified to express a Fc receptor such as CD16 (FcγRIII-A), or more generally, any other Fc receptor, on the surface of the cell.

In a first aspect, the invention is directed to NK-92 cells modified to express a Fc receptor on a surface of the cell; the Fc receptor can be an activating Fcγ receptor, CD16 (FcγRIII-A), or any member of an Fc receptor class, such as FCγRI (CD64), FCγRII (CD32), FCγRIII, FcRn, Fcα and Fcε. The Fc receptors can be of any binding affinity for their ligands, or fragments of their ligands, including low- and high-binding affinity forms. The NK-92 cells can be modified by introducing a polynucleotide that encodes a polypeptide having at least 70%, 80%, 90%, 95%, 99% or 100% identity to the amino acid sequences of SEQ ID NO:1 or SEQ ID NO:2; one such polynucleotide includes SEQ ID NO:3. The NK-92 cells can be further modified to express one or more associated accessory signaling polypeptides, cytokines, or fragments thereof; such expression can correlate with increased surface expression of the Fc receptor. Associated accessory signaling polypeptides include FcεRI-γ (SEQ ID NO:5) or TCR-ζ (SEQ ID NO:7). Expression of a cytokine (such as interleukin-2) can also correlate with viability or cytotoxicity of the modified NK-92 cells.

In a second aspect, the invention is directed to methods for in-vitro assessment of the efficacy of an antibody to induce cell death. Such methods can include the steps of exposing a target cell to an antibody (monoclonal (purified or in hybridoma supernates), polyclonal, chimeric (such as one having at least two dissimilar antigen binding domains (wherein one binding domain can be adapted to bind the Fc receptor), or any other form of antibody), exposing the target cell to a modified NK-92 cell expressing an Fc receptor; and then monitoring the target cell for cytotoxicity, cytolysis, or apoptosis, or a combination thereof. Pluralities of cells and antibodies can be used. The target cells used in the methods can have a lysis or aptotic rate of about 5%-30% in the presence of the modified NK-92 cells in the absence of antibody. Effector:target ratios include 0.5:1 to 100:1, including 1:1 and 20:1. Target cells in the methods include SKOV-3, P815, THP-1, U373MG, T98G, A ML193, SR91, ALL1, and REH; these and any other target cells can be modified to increase expression of the antigen to which the antibody binds. Appropriate negative controls include using unmodified NK-92 cells.

The NK-92 cells in this aspect can include those modified to express a Fc receptor on a surface of the cell; the Fc receptor can be an activating Fcγ receptor, CD16 (FcγRIII-A), or any member of an Fc receptor class, such as FCγRI (CD64), FCγRII (CD32), FCγRIII, FcRn, Fcα and Fcε. The Fc receptors can be of any binding affinity for their ligands, or fragments of their ligands, including low- and high-binding affinity forms. The NK-92 cells can be modified by introducing a polynucleotide that encodes a polypeptide having at least 70%, 80%, 90%, 95%, 99% or 100% identity to the amino acid sequences of SEQ ID NO:1 or SEQ ID NO:2; one such polynucleotide includes SEQ ID NO:3. The NK-92 cells can be further modified to express one or more associated accessory signaling polypeptides, cytokines, or fragments thereof; such expression can correlate with increased surface expression of the Fc receptor. Associated accessory signaling polypeptides include FcεRI-γ (SEQ ID NO:5) or TCR-ζ (SEQ ID NO:7). Expression of a cytokine (such as interleukin-2) can also correlate with viability or cytotoxicity of the modified NK-92 cells. Cytokines can also be added to the assay from exogenous sources.

In a third aspect, the invention is directed to methods for detecting cytolytic and apoptosis-inducing activity, the method including the steps of exposing a target cell in the absence of antibodies to a NK-92 cell expressing an Fc receptor, and then monitoring the target cell for cytotoxicity, cytolysis or apoptosis. Monitoring can include determining IFN-γ or cytokine expression levels. The method can further include applying blocking agents, such as activating receptor-masking antibodies or polypeptides (or fragments of these) to suppress one or more activating receptors on the NK-92 cell.

In a fourth aspect, the invention is directed to methods of assaying the efficacy of an antibody to treat a tumor, infection or other lesion, the method including the steps of administering an antibody (or plurality of antibodies) to a subject; administering modified NK-92 cells expressing an Fc receptor to the subject; and then monitoring the tumor, infection or lesion. The efficacy of the antibody in the treatment correlates with suppression of the tumor, infection or lesion in the subject. Monitoring can include determining IFN-γ or cytokine expression levels. The method can further include applying blocking agents, such as activating receptor-masking antibodies or polypeptides (or fragments of these) to suppress one or more activating receptors on the NK-92 cell.

The antibody can be monoclonal (purified or in hybridoma supernates), polyclonal, chimeric (such as one having at least two dissimilar antigen binding domains (wherein one binding domain can be adapted to bind the Fc receptor), or any other form of antibody. Cytokines (such as interleukin-2), or fragments thereof, can be expressed from modified NK-92 cells or supplied exogenously. Subjects include bovines (e.g., cows), swine (e.g., pigs, hogs), rabbits, alpacas, horses, canines (e.g., dogs), felines (e.g., cats), ferrets, rats, mice, fowl (chickens, turkeys) and buffalo. Subjects can also be human.

The NK-92 cells in this aspect can include those modified to express a Fc receptor on a surface of the cell; the Fc receptor can be an activating Fcγ receptor, CD16 (FcγRIII-A), or any member of an Fc receptor class, such as FCγRI (CD64), FCγRII (CD32), FCγRIII, FcRn, Fcα and Fcε. The Fc receptors can be of any binding affinity for their ligands, or fragments of their ligands, including low- and high-binding affinity forms. The NK-92 cells can be modified by introducing a polynucleotide that encodes a polypeptide having at least 70%, 80%, 90%, 95%, 99% or 100% identity to the amino acid sequences of SEQ ID NO:1 or SEQ ID NO:2; one such polynucleotide includes SEQ ID NO:3. The NK-92 cells can be further modified to express one or more associated accessory signaling polypeptides, cytokines, or fragments thereof; such expression can correlate with increased surface expression of the Fc receptor. Associated accessory signaling polypeptides include FcεRI-γ (SEQ ID NO:5) or TCR-ζ (SEQ ID NO:7).

In yet another, fifth aspect, the invention is directed to methods of treating a subject, the subject having a tumor, infection or other lesion, the method including administering to a subject antibodies that specifically bind to the tumor, infection or other lesion; and then administering to the subject modified NK-92 cells expressing an Fc receptor. A reduction in the tumor, infection or lesion indicates a therapeutic response. Monitoring can include determining IFN-γ or cytokine expression levels. The method can further include applying blocking agents, such as activating receptor-masking antibodies or polypeptides (or fragments of these) to suppress one or more activating receptors on the NK-92 cell.

The antibody can be monoclonal (purified or in hybridoma supernates), polyclonal, chimeric (such as one having at least two dissimilar antigen binding domains (wherein one binding domain can be adapted to bind the Fc receptor), or any other form of antibody. Cytokines (such as interleukin-2), or fragments thereof, can be expressed from modified NK-92 cells or supplied exogenously. Subjects include bovines (e.g., cows), swine (e.g., pigs, hogs), rabbits, alpacas, horses, canines (e.g., dogs), felines (e.g., cats), ferrets, rats, mice, fowl (chickens, turkeys) and buffalo. Subjects can also be human.

The NK-92 cells in this aspect can include those modified to express a Fc receptor on a surface of the cell; the Fc receptor can be an activating Fcγ receptor, CD16 (FcγRIII-A), or any member of an Fc receptor class, such as FCγRI (CD64), FCγRII (CD32), FCγRIII, FcRn, Fcα and Fcε. The Fc receptors can be of any binding affinity for their ligands, or fragments of their ligands, including low- and high-binding affinity forms. The NK-92 cells can be modified by introducing a polynucleotide that encodes a polypeptide having at least 70%, 80%, 90%, 95%, 99% or 100% identity to the amino acid sequences of SEQ ID NO:1 or SEQ ID NO:2; one such polynucleotide includes SEQ ID NO:3. The NK-92 cells can be further modified to express one or more associated accessory signaling polypeptides, cytokines, or fragments thereof; such expression can correlate with increased surface expression of the Fc receptor. Associated accessory signaling polypeptides include FcεRI-γ (SEQ ID NO:5) or TCR-ζ (SEQ ID NO:7).

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings.

DETAILED DESCRIPTION OF THE INVENTION

Figure 1A:
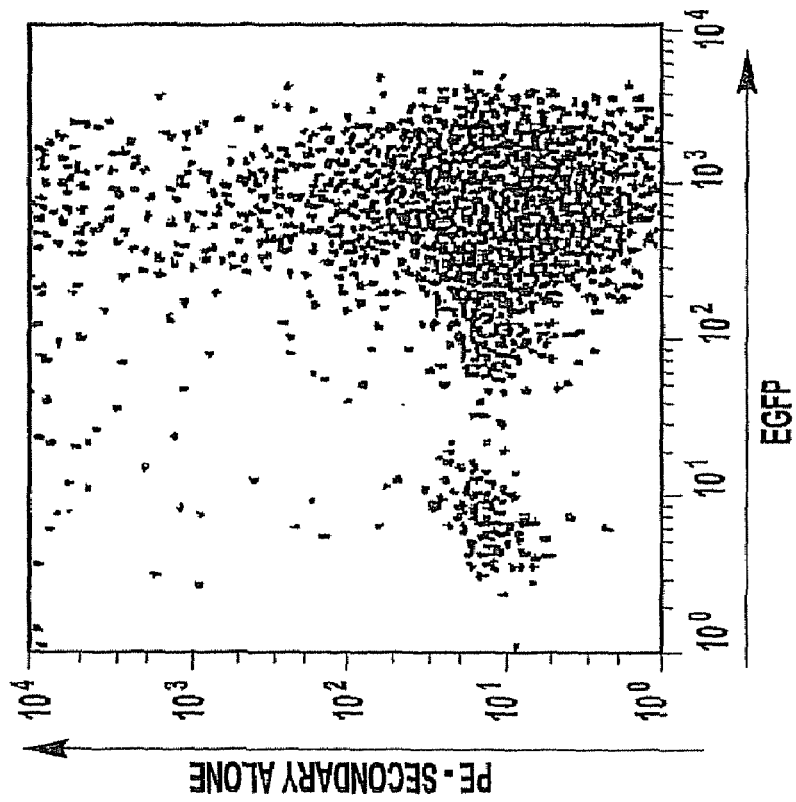
FIG. 1 shows flow cytometer scatter diagrams of NK-92 cells transduced with CD16 cDNA using the pBMN-IRES-EGFP vector after staining with no primary antibody (FIG. 1A) and with both primary (anti-CD16) and secondary antibody (FIG. 1B). EGFP expression is assessed on the x-axis, and surface CD16 expression is on the y-axis.

While the present invention is susceptible of embodiment in many different forms, there are shown in the drawings, and will be described herein in detail specific embodiments and examples thereof, with the understanding that the present disclosure is to be considered as an exemplification of the principles of the invention and is not intended to limit the invention to the specific embodiments illustrated.

The present invention is directed towards cell lines and methods that potentiate and broaden the effective scope of the ADCC response. The present invention provides an NK-92 cell line that stably expresses an Fc cell surface receptor protein, such as CD16. (Several different nomenclatures have evolved to refer to certain Fc receptors; they are used interchangeably herein, including CD16, FCγRIII-A, and their polymorphisms or other forms having varied affinity levels).

Many biotechnology companies are presently developing novel monoclonal antibodies for use in cancer immuno-therapies. The intent of this development effort is to prepare antibodies that bind to particular protein antigens that are uniquely expressed on the surfaces of specific types of tumor cells. Cytotoxic NK cells can, in turn, bind to the Fc (constant) region of these tumor-bound antibodies via the CD16 receptors displayed on the NK cells and initiate lysis of the tumor cell through the ADCC mechanism. The high efficacy and specificity of therapeutic agents based upon this approach has been clinically demonstrated through the use of the monoclonal antibody Herceptin (anti-ErbB2) for the treatment of ErbB2-expressing breast carcinomas and the use of the monoclonal antibody Rituximab (anti-CD20) for the treatment of B-cell lymphomas. Numerous other therapeutic antibodies that target a wide variety of additional tumor-specific antigens are under development.

An essential part of the development of antibody-based cancer therapies is the in-vitro determination of the efficacy and specificity of NK cell-mediated ADCC that is imparted by the binding of the antibody to the target tumor cell. These tests are typically conducted using peripheral blood lymphocytes (PBL) obtained from normal human donors or NK cells isolated from the PBL blood fraction as effector cells. In addition to the cumbersome burden inherent in routinely obtaining and processing human blood samples, there is considerable variability in the activity and quantity of effector cells obtained from different donors and similar variability between samples obtained from the same donor. Part of this variability is intrinsic and arises from the polyclonal nature of NK cells. In particular, allelic variations in the extracellular portion of the CD16 gene can result in significant differences in CD16 affinity for the Fc portions of antibodies and differences in the activation status of donor NK cells can alter the level of CD16 expression on the cell surface. The concentration of NK cells in the PBL fraction also varies, partly for genetic reasons and partly as a reflection of the physiological status of the donor. This effector cell variability greatly complicates the assessment of monoclonal antibodies as potential therapeutic agents. Furthermore, although NK cells expressing the low binding affinity form of CD16 are most common, the high affinity isotype is sufficiently common that antibody testing needs to be carried using NK cells of both forms (Koene et al., 1997). Identifying donors homozygous for low and high affinity allelic forms of CD16 is a difficult task. The availability of a clonal human NK cell population that expresses a consistent level of CD16 activity would provide substantial benefit as a standard effector in the evaluation of antibodies for ADCC activity and specificity.

In like manner, antibody-based therapies can benefit from the presence of NK cells having known high levels of Fc-binding capacity and cytotoxic activity within the subject. In addition to the variabilities previously described, NK cells isolated from cancer subjects are often found to have been rendered defective, deficient or ineffective by actions of the tumor cells. Some types of tumor cells, for example, are able to kill or deactivate NK cells in a subject-specific manner. Other types of tumor cells similarly are able to interfere with NK cell production, activity and/or specificity. Such variability makes reliance on subject NK cells problematic in a therapeutic setting and suggests that the co-administration of known quantities of exogenous NK cells having a known level of activity along with an appropriate antibody can result in more consistent therapeutic effects. Again, the availability of a clonal human NK cell population that expresses a consistent level of CD16 activity is expected to provide substantial benefit.

One major limitation on the usefulness of NK cells is that they express a repertoire of cell surface receptors that, when bound to the corresponding MHC-I ligand on a normal target cell, strongly and specifically prevent destruction of the target cell by inhibiting NK cell activation, cytotoxicity and cytokine response. This inhibition can abrogate the activation of NK cells caused by the binding of NK cell activating receptors to their conjugate ligands on the target cell. Thus a NK cell will destroy a target cell that displays only activating ligands, but will spare a target cell that displays MHC-I inhibitory ligands even if activating ligands are also present.

Almost all cells in mammals display certain polymorphic cell surface proteins of the MHC-I on their surfaces. These MHC-I proteins have the primary function of displaying peptide antigens that are fragments derived from proteins expressed within a cell and are classified as being MHC-I complexes. The MHC complexes displayed on normal cells are unique to each individual and are often referred to as being markers of "self" for that individual. Exogenous cells introduced by transplantation display MHC molecules and associated peptides that differ from those of the host individual and are therefore referred to as being "non-self." Non-self MHC-peptide complexes can also appear on aberrant cells as a result of processes that alter the peptides presented on the MHC molecules. In particular, non-self peptides are displayed by many, but not all, tumor cells and infected cells.

NK cell inhibitory receptors consist of several families of proteins that recognize, bind to and are triggered to send "negative intracellular signals" by encountering intact self MHC-I proteins on the surface of a normal self, target cell. NK cells are therefore prevented from attacking and destroying normal cells that display the appropriate self MHC-I constellation. Tumor and infected cells that display this self MHC-I constellation are also immune from attack. Only cells that display non-self or no MHC-I are subject to destruction by NK cells. Some types of tumor and infected cells that do not display self MHC-I complexes have, however, evolved mechanisms that allow them to escape this fate. Examples of such escape mechanisms include expression of surrogate MHC-1-like, NK cell inhibitory receptor ligands and the secretion of soluble ligands that suppress NK cell functions. Tumor and infected cells that implement such escape mechanisms are refractory to NK cell-mediated lysis. The efficacy of NK cells as an agent for the destruction of cancer cells is therefore limited by the presence of appropriate MHC-I ligands for NK cell inhibitory receptors. The availability of a human NK cell population that does not express NK cell inhibitory receptors would beneficially expand the range of cancers and infections that can be treated using antibody-based therapeutic agents.

NK-92 is a NK-like cell line that was initially isolated from the blood of a subject suffering from a large granular lymphoma and subsequently propagated in cell culture. The NK-92 cell line has been described (Gong et al., 1994; Klingemann, 2002). NK-92 cells have a CD3−/CD56+ phenotype that is characteristic of NK cells. They express all of the known NK cell-activating receptors except CD16, but lack all of the known NK cell inhibitory receptors except NKG2A/CD94 and ILT2/LIR1, which are expressed at low levels. Furthermore, NK-92 is a clonal cell line that, unlike the polyclonal NK cells isolated from blood, expresses these receptors in a consistent manner with respect to both type and cell surface concentration. Similarly, NK-92 cells are not immunogenic and do not elicit an immune rejection response when administered therapeutically to a human subject. Indeed NK-92 cells are well tolerated in humans with no known detrimental effects on normal tissues. While NK-92 cells, unlike NK cells and cells of most of the other known NK-like cell lines, have been engineered to express novel proteins by means of transduction using retroviral vectors (Campbell et al., 2004; Kikuchi-Maki et al., 2003; Klingemann, 2002; Yusa and Campbell, 2003; Yusa et al., 2002; Yusa et al., 2004), such engineering has proved difficult as evidenced by numerous failures to engineer NK-92 cells to express an Fc receptor. More particularly, despite the clear potential benefits which could be anticipated from an NK-92 cell line modified to express CD16, such genetic modification had not been achieved in fact until the present invention.

This unique combination of characteristics renders NK-92 as a suitable platform upon which the present invention can be constructed. In particular, the lack of inhibitory receptors means that NK-92 cells are not MHC-restricted and can act effectively against any cell that displays an appropriate activating ligand independent of any MHC-I inhibitory ligands that can also be expressed. The lack of immunogenicity coupled with the relative ease with which NK-92 cells can be grown in culture means that they can be prepared in bulk and administered to any subject as the need arises. The stability and consistency of NK-92 cells males them suitable for use as a reference material and therapeutic agent. In addition, the present invention provides the ability to transduce NK-92 cells with genes for novel proteins, such as Fc receptors, in conjunction with the ability of NK-92 cells to stably express these proteins, as explained in greater detail below.

The use of NK-92 cells as a therapy for cancers is currently being evaluated with promising results in human clinical trials. The benefits of NK-92 cells are being further exploited through the development of genetically engineered NK-92 variants that express a protein construct that covalently links an antibody-like binding domain to a signaling domain such as TCR-ζ (Genbank Accession No. J04132; SEQ ID NO:6) (TCR-ζ (Genbank Accession No. J04132; SEQ ID NO:6)) (Klingemann, 2002; Maki et al., 2001; Uherek et al., 2001; Uherek et al., 2002). In these constructs, the antibody-like domain is structured to specifically bind to an antigen that is expressed by a target cell while the signaling domain is one that is known to trigger NK and NK-92 cell activity when stimulated. It has, to date, been demonstrated in-vitro and in animal models that the binding of the antibody-like domain of such a construct to its antigen on a target cell triggers the NK-92 cell in a manner such that it rapidly and efficiently destroys the target cell via direct conjugation. The utility of these constructs as therapeutic agents is, however, limited by the need to design, prepare and validate a unique construct for each specific type of cancer or infection to be treated. The availability of a single NK-92 cell variant that can be used to treat a broad range of cancers and infections is of beneficial utility.

One area in which NK-92 cells can be improved pertains to the use of NK-92 cells in subjects, in that the cytotoxicity, cell surface receptor concentration and survival of NK-92 cells as well as the range of tumor and infected cell types that are attacked have been shown to be increased by the presence of low concentrations of the cytokine interleukin-2 (IL-2). The cost of the exogenously added IL-2 needed to maintain and expand NK-92 cells in commercial scale culture is significant, while the administration of IL-2 to human subjects in sufficient quantity to achieve the desired effects is also known to cause adverse side effects. This limitation has been addressed by the development of the IL-2 secreting NK-92 ml and NK-92ci cell lines by retroviral transduction of NK-92 cells with the gene for IL-2 (Klingemann, 2002; Nagashima et al., 1998). The levels of IL-2 secreted by these cell lines are sufficient to optimize NK-92 cell survival and activity, but are below the level generally associated with the onset of adverse side effects.

Another area in which NK-92 cells can be improved, and the focus of the present invention, concerns the fact that an unmodified NK-92 cell does not express CD16 and therefore is ineffective in killing target cells via the ADCC mechanism. Although NK-92 cells are widely used as a model system for the study of NK cell activation, action and inhibition, the lack of CD16 expression precludes the use of NK-92 cells for the evaluation of efficacy of antibodies as therapeutic agents and the use of NK-92 cells as a therapeutic agent that is co-administered with an antibody. The present invention addresses this limitation by causing NK-92 cells to express CD16. Additional utility and benefit of the present invention will become apparent in the following descriptions.

Modifying NK-92 Cells

CD16 is most commonly found in a form that has a relatively low binding affinity for the Fc portion of IgG molecules. An alternative form that exhibits a higher binding affinity is found in some individuals. The low and high affinity forms of CD16 differ only by the substitution of valine (high affinity) for phenylalanine (low affinity) at position 157 in the polypeptide chain. The complete sequences of the low and high affinity forms can be found in the SwissProt database as entries P08637 (SEQ ID NO:1) and VAR_008801 (SEQ ID NO:2), respectively and are presented in Tables 1 and 2; the polynucleotide encoding SEQ ID NO:1 (SEQ ID NO:3) is presented in Table 3.

CD16 was introduced into NK-92 cells by means of retroviral transduction in the following manner. Complementary DNA encoding the gene for either the low or high affinity form of CD16 was sub-cloned into a bi-cistronic retroviral expression vector, pBMN-IRES-EGFP (obtained from G. Nolan, Stanford University, Stanford, Calif.) using the BamHI and NotI restriction sites in accordance with standard methods (e.g., (Ausubel, 2002; Sambrook and Russell, 2001)). This expression vector was then transfected into the Phoenix-Amphotropic retroviral packaging cell line and the resulting virus-containing supernate was used to transduce NK-92 cells, although alternative methods including those in which vectors incorporate EGFP or other fluorescent proteins (yellow, red, cyan, etc.) can be used without departing from the spirit and scope of this invention, and the Phoenix-Amphotropic retroviral packaging cell line were both obtained from and are available to the public from the Leland Stanford University, Stanford, Calif., USA; (Kinsella and Nolan, 1996; Nolan and Kinsella, 1998)). As indicated below, other vectors and packaging cell lines, both those currently known and those which can be developed in the future, can be used. Transduced NK-92 cells expressing CD16 on their surface (NK-92-CD16, also known as CD16/FcεRIγ-NK-92) were separated from the residual non-transduced NK-92 cells using a fluorescence activated cell sorter (FACS). When appropriate to the intended use, the NK-92-CD16 cells were further sub-sorted on the basis of CD16 expression level using a FACS, based upon coordinate expression of Enhanced Green Fluorescent Protein (EGFP). The resulting NK-92-CD16 cells stably express CD16 in cell culture without the need for periodic antibiotic selection.

TABLE 1

Polypeptide sequence for SEQ ID NO: 1 (Low affinity immunoglobulin gamma Fc region receptor III-A [Precursor]) (F176)

| Met | Trp | Gln | Leu | Leu | Leu | Pro | Thr | Ala | Leu | Leu | Leu | Leu | Val | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Met | Arg | Thr | Glu | Asp | Leu | Pro | Lys | Ala | Val | Val | Phe | Leu | Glu | Pro |
|-----|-----|-----|-----|-----|-----|-----|-----|-----|-----|-----|-----|-----|-----|-----|-----|
|     |     |     | 20  |     |     |     |     | 25  |     |     |     |     |     | 30  |     |

TABLE 1-continued

Polypeptide sequence for SEQ ID NO: 1 (Low affinity immunoglobulin gamma Fc region receptor III-A [Precursor]) (F176)

Gln Trp Tyr Arg Val Leu Glu Lys Asp Ser Val Thr Leu Lys Cys Gln
                35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Gys
                115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
                195                 200                 205

Val Ser Phe Cys Leu Val Met Val Leu Leu Phe Ala Val Asp Thr Gly
                210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

TABLE 2

Polypeptide sequence for SEQ ID NO: 2 (High affinity variant F176V immunoglobulin gamma Fc region receptor III-A [Precursor])

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
                35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
                115                 120                 125

His Ser Trp Lys Asn Thr Ala Leu His Lys Val Thr Tyr Leu Gln Asn
        130                 135                 140

TABLE 2-continued

Polypeptide sequence for SEQ ID NO: 2 (High affinity variant F176V immunoglobulin gamma Fc region receptor III-A [Precursor])

```
Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

TABLE 3

Polynucleotide sequence (mRNA) for SEQ ID NO: 3 (Low affinity immunoglobulin gamma Fc region receptor III-A [Precursor])

```
atgtggcagc tgctcctccc aactgctctg ctacttctag tttcagctgg catgcggact    60
gaagatctcc caaaggctgt ggtgttcctg gagcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gtcgacgaca gtgagagta caggtgccag acaaacctct ccaccctcag tgacccggtg    300
cagctagaag tccatatcgg ctggctgttg ctccaggccc tcggtgggt gttcaaggag   360 gaagaccccta ttcacctgag gtgtcacagc tggaagaaca ctgctctgca taaggtcaca   420
tatttacaga atggcaaagg caggaagtat tttcatcata attctgactt ctacattcca   480
aaagccacac tcaaagacag cggctcctac ttctgcaggg ggcttttttgg gagtaaaaat   540 gtgtcttcag agactgtgaa catcaccatc actcaaggtt tggcagtgtc aaccatctca   600
tcattctttc cacctgggta ccaagtctct ttctgcttgg tgatggtact ccttttttgca   660 gtggacacag gactatattt ctctgtgaag acaaacattc gaagctcaac aagagactgg   720
aaggaccata aatttaaatg gagaaaggac cctcaagaca aatga                   765
```

Recombinant Expression Vectors and Host Cells

Vectors are tools used to shuttle DNA between host cells or as a means to express a polynucleotide sequence. Inserting the DNA of interest, such as a CD16 sequence or a fragment, is accomplished by ligation techniques and/or mating protocols well known to the skilled artisan. Such DNA is inserted such that its integration does not disrupt any necessary components of the vector. In the case of vectors that are used to express the inserted DNA as a polypeptide, the introduced DNA is operably-linked to the vector elements that govern its transcription and translation.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors. Operably-linking a CD16 polynucleotide to an inducible promoter can control the expression of a CD16 gene or fragments. Examples of inducible promoters include those that are tissue-specific, which relegate expression to certain cell types, steroid-responsive (e.g., glucocorticoids (Kaufman, 1990) and tetracycline), or heat-shock reactive. Some bacterial repression systems, such as the lac operon, have been exploited in mammalian cells and transgenic animals (Fieck et al., 1992; Wyborski et al., 1996; Wyborski and Short, 1991). Other desirable inducible promoters include those that are not endogenous to the cells in which the construct is being introduced, but, however, are responsive in those cells when the induction agent is exogenously supplied.

Vectors have many manifestations. A "plasmid" is a circular double stranded DNA molecule that can accept additional DNA fragments. Viral vectors can also accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) integrate into the genome of a host cell and replicate as part of the host genome. In general, useful expression vectors are plasmids and viral vectors (e.g., replication defective retroviruses, adenoviruses and adeno-associated viruses); other expression vectors can also be used.

Vector choice is dictated by the organisms or cells being used and the desired fate of the vector. Vectors can replicate once in the target cells, or can be "suicide" vectors. In general, vectors comprise signal sequences, origins of replication, marker genes, enhancer elements, promoters, and transcription termination sequences. Vectors often use a selectable marker to facilitate identifying those cells that have incorporated the vector. Table F summarizes many of the available markers.

"Host cell" and "recombinant host cell" are used interchangeably. Such terms refer not only to a particular subject fection, as well as established genetic techniques, if any, for that particular organism. Such procedures can similarly be employed for the transduction of genetically engineered NK-92 cells, including NK-92-CD16-γ, NK-92-CD16-ζ, NK-92 ml and NK-92ci. The NK-92, NK-92 ml and NK-92ci cell lines are deposited with the American Type Culture Collection (ATCC, 10801 University Boulevard, Manassas, Va. 20110-2209) under Deposit Numbers CRL-2407 (deposited to general depository on Sep. 3, 1998; transferred to patent depository on Apr. 11, 2005 and assigned Deposit No. PTA-6670), CRL-2408 and CRL-2409, respectively. No-GFP-CD16.NK-92 cell line (high affinity; 176V; SEQ ID NO:2) was deposited with ATCC on Sep. 9, 2005 and was assigned Accession No. PTA-6967. GFP-CD16-F/F.NK-92 (low affinity; SEQ ID NO:1) and GFP-CD16-V/V.NK-92 cell line (high affinity; SEQ ID NO:2) were deposited with ATCC on Dec. 13, 2007. Viability testing In conjunction with Amendment and Response to Non-Final Office Action was completed, and a Certificate of Deposit was issued by the ATCC on Feb. 14, 2008, for the low affinity cell line which was assigned ATCC Patent Deposit Designation No. PTA-8837. Viability testing was completed, and a Certificate of Deposit was issued by the ATCC on Feb. 13, 2008, for the high affinity cell line which was assigned ATCC Patent Deposit Designation No. PTA-8836.

TABLE A

Methods to introduce polynucleotide into cells

| Cells | Methods | References | Notes |
| --- | --- | --- | --- |
| Mammalian cells | Calcium phosphate transfection | N-(2-Hydroxyethyl)piperazine-N'-(2-ethanesulfonic acid (HEPES) buffered saline solution (Chen and Okayama, 1988; Graham and van der Eb, 1973; Wigler et al., 1978) BES (N,N-bis(2-hydroxyethyl)-2-aminoethanesulfonic acid) buffered solution (Ishiura et al., 1982) | Cells may be "shocked" with glycerol or dimethylsulfoxide (DMSO) to increase transfection efficiency (Ausubel, 2002). |
| | Diethylaminoethyl (DEAE)-Dextran transfection | (Fujita et al., 1986; Lopata et al., 1984; Selden et al., 1986) | Most useful for transient, but not stable, transfections. Chloroquine can be used to increase efficiency. |
| | Electroporation | (Neumann et al., 1982; Potter, 1988; Potter et al., 1984; Wong and Neumann, 1982) | Especially useful for hard-to-transfect lymphocytes. |
| | Cationic lipid reagent transfection | (Elroy-Stein and Moss, 1990; Felgner et al., 1987; Rose et al., 1991; Whitt et al., 1990) | Applicable to both in vivo and in vitro transfection. |
| | Retroviral | Production exemplified by (Cepko et al., 1984; Miller and Buttimore, 1986; Pear et al., 1993) Infection in vitro and in vivo: (Austin and Cepko, 1990; Bodine et al., 1991; Fekete and Cepko, 1993; Koehne et al., 2003; Lemischka et al., 1986; Turner et al., 1990) | Lengthy process, many packaging lines available at ATCC. Applicable to both in vivo and in vitro transfection. |
| | Polybrene | (Chaney et al., 1986; Kawai and Nishizawa, 1984) | |
| | Microinjection | (Capecchi, 1980) | Can be used to establish cell lines carrying integrated copies of DFF DNA sequences. |
| | Protoplast fusion | (Rassoulzadegan et al., 1982; Sandri-Goldin et al., 1981; Schaffner, 1980) | | cell but also to the progeny or potential progeny of such a cell. Because certain modifications may occur in succeeding generations due to either mutation or environmental influences, such progeny may not, in fact, be identical to the parent cell, but are still included within the scope of the term.

Methods of eukaryotic cell transfection and prokaryotic cell transformation are well known in the art (see examples in Table B). The choice of host cell dictates the preferred technique for introducing the polynucleotide of interest. Introduction of polynucleotides into an organism may also be done with ex vivo techniques that use an in vitro method of trans- Other vectors and packaging cell lines have been used in the preparation of genetically modified variants of NK-92 cells (Klingemann, 2002; Nagashima et al., 1998; Tam et al., 1999; Uherek et al., 2002) and can be used equivalently herein. Retroviral transduction systems other than those of the Examples discussed below have also been successfully used to transduce a variety of genes into NK-92 cells. By way of example, these alternative methods include, but are not limited to the p-JET vector in conjunction with FLYA13 packaging cells (Gerstmayer et al., 1999), the plasmid-based kat retroviral transduction system, and DFG-hIL-2-neo/CRIP (Nagashima et al., 1998). Electroporation and "gene gun" introduction of the vector into the packaging cells is also practiced. Use of the pBMN-IRES-EGFP vector in combination with the Phoenix-Amphotropic packaging cell line is convenient for the purpose of this and the following Examples in that it provides high efficiencies of Phoenix-Amphotropic cell transfection; the use of Moloney LTR promoters results in a high level of CD16 expression; the virus is produced at high titers; the efficiency of NK-92 transduction is improved over other vectors that have been used to transduce NK-92; and the vector provides adequate space to accommodate the CD16 cDNA or alternative inserts. The pBMN-IRES-EGFP vector further incorporates genes for enhanced green fluorescent protein (EGFP), which can be used as an endogenous surrogate marker for gene expression. The *Phoenix* cell line stably expresses this vector in episomal form along with producing other viral components, thus allowing the cells to stably produce virus for an extended period of time. Importantly, previously described publications (Klingemann, 2002; Nagashima et al., 1998; Tam et al., 1999; Uherek et al., 2002) have established that alternative retroviral systems can be used to introduce cDNAs into NK-92 without departing from the spirit and scope of the invention.

A "homologous polynucleotide sequence" or "homologous amino acid sequence," or variations thereof, refer to sequences characterized by a homology at the polynucleotide level or amino acid level. Homologous polynucleotide sequences encode those sequences coding for isoforms of CD16. Different genes can encode isoforms such as homologous CD16 polynucleotide sequences of species other than mice, including other vertebrates, such as human, frog, rat, rabbit, dog, cat, cow, horse, and other organisms. Homologous polynucleotide sequences also include naturally occurring allelic variations and mutations of SEQ ID NOs:1 or 2. Homologous polynucleotide sequences may encode conservative amino acid substitutions in SEQ ID NOS:1 or 2.

The invention further encompasses using CD16 polynucleotide molecules that differ from the polynucleotide sequence shown in SEQ ID NO:3, due to degeneracy of the genetic code and thus encode the same CD16 as that encoded by the polynucleotide sequence shown in SEQ ID NO:3. Any polynucleotide molecule encoding a polypeptide having an amino acid sequence shown in SEQ ID NOS:1 or 2 is useful for modifying NK-92 cells.

In addition to the CD16 polynucleotide sequence shown in SEQ ID NO:3, DNA sequence polymorphisms that change the CD16 amino acid sequences can also be useful to modify NK-92 cells. For example, allelic variations among individuals exhibit genetic polymorphisms in CD16 genes.

Moreover, CD16 genes from other species that have a polynucleotide sequence that differs from the sequence of SEQ ID NO:3 are contemplated to be useful in the compositions and methods of the invention.

"CD16 variant polynucleotide" or "CD16 variant polynucleotide sequence" means a polynucleotide molecule which encodes a CD16 polypeptide that (1) has at least about 70% polynucleotide sequence identity with a polynucleotide acid sequence encoding a full-length native CD16, (2) a full-length native CD16 lacking the signal peptide, (3) an extracellular domain of a CD16, with or without the signal peptide, or (4) any other fragment of a full-length CD16. Ordinarily, a CD16 variant polynucleotide will have at least about 70% polynucleotide sequence identity, more preferably at least about 71%-99% polynucleotide sequence identity and yet more preferably at least about 75%, 80%, 85%, 90%, 91%, 92%, 93%, 94%, 95%, 96%, 97%, 98% and even more preferably, 99% polynucleotide sequence identity with the polynucleotide sequence encoding a full-length, native CD16. A CD16 variant polynucleotide can encode full-length native CD16 lacking the signal peptide, an extracellular domain of CD16, with or without the signal sequence, or any other fragment of a full-length CD16.

Ordinarily, CD16 variants are at least about 30 polynucleotides, often at least about 60, 90, 120, 150, 180, 210, 240, 270, 300, 450, 600 polynucleotides in length, more often at least about 900 polynucleotides in length, or more.

"Percent (%) polynucleotide sequence identity" with respect to CD16-encoding polynucleotide sequences is defined as the percentage of polynucleotides in the CD16 polynucleotide sequence of interest that are identical with the polynucleotides in a candidate sequence, after aligning the sequences and introducing gaps, if necessary, to achieve the maximum percent sequence identity. Alignment can be achieved in various ways well-known in the art; for instance, using publicly available software such as BLAST, BLAST-2, ALIGN or Megalign (DNASTAR) software. Those skilled in the art can determine appropriate parameters for measuring alignment, including any necessary algorithms to achieve maximal alignment over the full length of the sequences being compared.

When polynucleotide sequences are aligned, the % polynucleotide sequence identity of a given polynucleotide sequence C to, with, or against a given polynucleotide sequence D (which can alternatively be phrased as a given polynucleotide sequence C that has or comprises a certain % polynucleotide sequence identity to, with, or against a given polynucleotide sequence D) can be calculated as:

$$\text{\% polynucleotide sequence identity} = W/Z \cdot 100$$

where

W is the number of polynucleotides scored as identical matches by the sequence alignment program's or algorithm's alignment of C and D and Z is the total number of polynucleotides in D.

When the length of polynucleotide sequence C is not equal to the length of polynucleotide sequence D, the % polynucleotide sequence identity of C to D will not equal the % polynucleotide sequence identity of D to C.

Homologs or other related sequences (e.g., paralogs) can be obtained by low, moderate or high stringency hybridization with all or a portion of the particular sequence used as a probe using polynucleotide hybridization and cloning methods well known in the art.

In addition to naturally-occurring allelic variants of CD16 polynucleotides, changes can be introduced by mutation into SEQ ID NO:3 that incur alterations in the amino acid sequence of CD16 but does not alter CD16 function for the purposes of the invention. For example, polynucleotide substitutions leading to amino acid substitutions at "non-essential" amino acid residues can be made in SEQ ID NOs:1 or 2. A "non-essential" amino acid residue is a residue that can be altered from the wild-type sequence of CD16 without altering CD16 function in the methods and compositions of the invention, whereas an "essential" amino acid residue is required for activity. For example, amino acid residues that are conserved among the CD16 amino acids of the invention are particularly non-amenable to alteration (Table 9).

Useful conservative substitutions are shown in Table B, "Preferred substitutions." Conservative substitutions whereby an amino acid of one class is replaced with another amino acid of the same type fall within the scope of the subject invention so long as the substitution does not materially alter the activity of the compound in the methods and compositions of the invention. If such substitutions result in such a change, then more substantial changes, indicated in Table C as exemplary, are introduced and the products screened for CD16 activity for the methods and compositions of the invention.

TABLE B

Preferred substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge or (3) hydrophobicity, or (4) the bulk of the side chain of the target site can modify CD16 polypeptide function or immunological identity. Residues are divided into groups based on common side-chain properties as denoted in Table A. Non-conservative substitutions entail exchanging a member of one of these classes for another class. Substitutions may be introduced into conservative substitution sites or more preferably into non-conserved sites.

TABLE C

| Amino acid classes | |
|---|---|
| Class | Amino acids |
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

CD16 Polypeptide Variants

"CD16 polypeptide variant" means a CD16 polypeptide having at least: (1) about 80% amino acid sequence identity with a full-length native CD16 sequence, (2) a CD16 sequence lacking a signal peptide, (3) an extracellular domain of a CD16, with or without a signal peptide, or (4) any other fragment of a full-length CD16 sequence. For example, CD16 variants include those wherein one or more amino acid residues are added or deleted at the N- or C-terminus of the full-length native amino acid sequence. A CD16 polypeptide variant will have at least about 80% amino acid sequence identity, preferably at least about 81% amino acid sequence identity, more preferably at least about 81%, 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native sequence CD16 sequence. Ordinarily, CD16 variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues that are identical with amino acid residues in a CD16 sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Publicly available computer software such as BLAST, BLAST2, ALIGN2 or Megalign (DNASTAR) can be used to align polypeptide sequences. Those skilled in the art will determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\%\text{ amino acid sequence identity}=X/Y\cdot 100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

A CD16 "chimeric polypeptide" or "fusion polypeptide" comprises CD16 fused to a non-CD16 polypeptide. A non-CD16 polypeptide is not substantially homologous to CD16 (SEQ ID NOs:1 or 2). A CD16 fusion polypeptide may include any portion to an entire CD16, including any number of biologically active portions.

Fusion polypeptides can be easily created using recombinant methods. A polynucleotide encoding CD16 (e.g., SEQ ID NO:3) can be fused in-frame with a non-CD16 encoding polynucleotide, to the CD16 N- or C-terminus, or internally. Fusion genes may also be synthesized by conventional techniques, including automated DNA synthesizers and PCR amplification using anchor primers that give rise to complementary overhangs between two consecutive gene fragments that can subsequently be annealed and reamplified to generate a chimeric gene sequence (Ausubel, 2002). Many vectors are commercially available that facilitate sub-cloning CD16 in-frame to a fusion moiety.

Measuring Cytoxicity Some examples of measuring cytoxicity are presented herein below, but any cytotoxicity assay can be used without departing from the spirit and scope of the invention.

NK-92-CD16 cells can be used in ADCC assays as a pure "effector" cell population having defined and consistent characteristics. In some instances it can be desirable to select and use cells that exhibit intermediate levels of CD16 expression. In particular, such intermediate cells can be of use in generating dose-response curves and as "ladder" type calibrators for CD16 activity. NK-92 cells transduced with the low and high affinity forms of CD16 could likewise be used for these purposes.

Such in-vitro assays are commonly employed for purposes such as the determination of the efficacy of antibodies that are being developed as potential therapeutic agents. ADCC assays are typically performed by loading target cells with an indicator material such as [$^{51}$Cr] or a Europium chelate; treating the indicator-loaded target cells with the antibody to be evaluated; and exposing these cells to NK-92-CD16 effector cells. Lysis of the target cells is indicated by the release of the indicator material into the assay supernate where its concentration can be measured by a suitable method such as scintillation counting ($^{51}$Cr) or fluorescence intensity or lifetime determination (Europium chelate). Efficacy can likewise be assessed by the measurement of surrogate indicators such as cytokine release by the NK-92-CD16 cells; the up-regulation of NK cell activation markers, such as CD25, CD69 and/or CD95L; activation of NK-92 cell transcription factors, such as NF-AT or NF-κB; or the activation of caspases or other markers of apoptosis in the target cells. CD16-deficient parental NK-92 cells serve as a unique and valuable control in such assays as they permit differentiating between ADCC-mediated cytotoxicity and other cytolytic effects that NK-92 cells exert on the target cells. The preferred target cells in ADCC assays are ones that express an antigen that is appropriate to the antibody being evaluated and that have low susceptibility to lysis by the parental NK-92 cell line. If such a target cell line is not conveniently available, other suitable cell lines, such as the ovarian carcinoma line SKOV-3 (e.g., ATCC Deposit HTB-77) (Tam et al., 1999), can sometimes be used as a viable substitute, particularly if transduced/transfected such that they express the specific antigen required. Among the cell lines that have been demonstrated to be suitable for use in assays of ADCC-mediated cytotoxicity are U373MG and T98G (e.g., ATCC Deposit CRL-1690) (Komatsu and Kajiwara, 1998); AML-193 (myeloid; e.g., ATCC Deposit CRL-9589) and SR-91 (lymphoid progenitor) (Gong et al., 1994); and ALL1 and REH (B-cell acute lymphocytic leukemia) (Reid et al., 2002). Other types of target cells such as the FcγRII/III$^+$ murine mastocytoma cell line P815 (e.g., ATCC Deposit No. TIB-64); and the FcγRII/III$^+$ myelocytic leukemia line THP-1 (e.g., ATCC Deposit No. TIB-202) that have limited (between 5 and 30%) susceptibility to lysis by unmodified NK-92 cells are preferably used where redirected cytotoxicity or ADCC is to be determined in order to ensure sufficient assay dynamic range for the detection of significant effects through CD16. Other cell types with limited cytolytic potential that express or are engineered to express specific cell surface markers of interest can also be employed as targets. Furthermore, the baseline cytolytic capacity of NK-92 cells can be reduced by either decreasing the IL-2 concentration in the cultures and/or assaying four days after passing the cells into fresh IL-2-containing medium. The functionality of CD16 introduced into NK-92-CD16, NK-92-CD16-γ or NK-92-CD16-ζ cells can be determined using the cytotoxicity assay of Example 4 in either the ADCC or the "redirected cytotoxicity" format. Monoclonal antibodies that bind CD16 can be used to test for function of the receptor on NK-92 cells in a redirected cytotoxicity assay, in which the antibody's F(ab) portion binds the receptor on the NK cell and the Fc portion binds to Fc receptors on appropriate target cells (FcγRII/III on P815 or THP-1 target cells). Another form of redirected cytotoxicity can be tested using a chimeric bi-specific antibody, such as 2B1 (Clark et al., 1997; Weiner et al., 1995a; Weiner et al., 1995b), which expresses two F(ab) regions, one which binds CD16 on the NK-92 cell and another that binds the Her2/neu antigen on an appropriate target cell line, such as SKOV-3. Furthermore, monoclonal antibodies that specifically bind antigens that are uniquely expressed on the target cells can directly test ADCC. In this format, the F(ab) portion of the antibody binds to the corresponding ligand on the target cell while the CD16 receptor on the NK-92-CD16 cells bind to the Fc portion of the antibody. The resulting cross-link between the antigen on the target cell and the CD16 receptor results in lysis of the target cell via the ADCC pathway.

For some purposes, particularly as related to the evaluation of bi- or poly-functional antibodies or in the study of activation mechanisms and other characteristics of NK-92 cells, it can be useful to restructure the previously described ADCC assay as a "redirected cytotoxicity" assay. For example, a bi-functional antibody having one domain that specifically binds to an antigen of interest on the target cells and a second domain that specifically binds to CD16 on NK-92-CD16 cells can be evaluated in the manner described above. In this instance, the bi-functional antibody cross-links the antigen on the target cell to CD16 on the NK-92-CD16 cell and triggers an ADCC response. The same assay for research purposes can, for example, treat a target cell that expresses CD16 or another Fc receptor with an antibody such as anti-CD16 that is directed against this receptor. Exposing the anti-CD16 labeled target cells to NK-92-CD16 cells results in the cross-linking of the receptors on both cells with consequent triggering of ADCC. Differentiation between the ADCC and redirected cytotoxicity formats is based upon whether the effector cell CD16 receptor binds to the Fc portion of an antibody (ADCC) or this same receptor is bound by the F(ab) portion of an anti-CD16 antibody (redirected cytotoxicity). As both binding arrangements can trigger similar cytotoxicity responses in the target cell, the choice between the ADCC and redirected formats is largely a matter of convenience.

In some instances, it can be advantageous to block known activating receptors on NK-92 cells; such methods and agents are well-known; see for example (Pende et al., 1999; Pessino et al., 1998; Vitale et al., 1998). For example, masking antibodies can be used (Pessino et al., 1998).

In the presence of an appropriate antibody, NK-92-CD16 cells can effectively and efficiently lyse target cells. CD16 in NK cells is non-covalently associated in the plasma membrane with homodimers or heterodimers of the FcεRI-γ (Genbank Accession No. M33195; SEQ ID NO:4 (polynucleotide) and SEQ ID NO:5 (polypeptide)) or TCR-ζ (Genbank Accession No. J04132; SEQ ID NO:6 (polynucleotide); SEQ ID NO:7 (polypeptide)) accessory signaling proteins; these sequences are presented in Tables 4-7. Discussion regarding sequence identity applies also to SEQ ID NOs:4-7; thus, those polynucleotides or polypeptides of SEQ ID NOs:4-7 having about at least 70%-100% sequence identity, as well as 80%-90%, and 81%, 82%, 83%, 84%, 85%, 86%, 87%, 88%, 89%, 90%, 91%, 92%, 93%, 94%, 95%, 96%, 97%, 98% and 99% sequence identity are useful for the methods and composition of the invention. When stimulated by the binding of Fc to CD16, these accessory signaling proteins can transduce intracellular signals that activate NK cell cytotoxicity and cytokine release activities. In addition, they support surface expression of CD16. The signaling activity initiated through ζ and γ serves to trigger ADCC responses. FcεRI-γ and/or TCR-ζ can conveniently be co-introduced into NK-92 cells by sequential transduction with CD16 and FcεRI-γ and/or TCR-ζ cDNA in the manner described above. In this process, it is generally desirable to delete the EGFP gene from the vector containing the CD16 cDNA. The sequential transduction process consists of transducing the parental NK-92 cells with the CD16 vector; immunostaining the transduced cells with a fluorescently labeled anti-CD16 antibody; sorting the cells for CD16 expression; transducing the NK-92-CD16 cells with a vector containing cDNA for both the accessory protein and EGFP; and sorting the doubly transduced cells on the basis of EGFP expression. The resulting doubly transduced NK-92 cells (NK-92-CD16/γ or NK-92-CD16/ζ, respectively) usually exhibit higher levels of surface CD16 expression and enhanced cytotoxicity and cytokine release activities than do NK-92-CD16 cells.

TABLE 4

FcεRI-γ polynucleotide sequence (SEQ ID NO: 4)

| | | | | | |
|---|---|---|---|---|---|
| cagaacggcc | gatctccagc | ccaagatgat | tccagcagtg | gtcttgctct | tactcctttt 60 |
| ggttgaacaa | gcagcggccc | tgggagagcc | tcagctctgc | tatatcctgg | atgccatcct 120 |
| gtttctgtat | ggaattgtcc | tcaccctcct | ctactgtcga | ctgaagatcc | aagtgcgaaa 180 |
| ggcagctata | accagctatg | agaaatcaga | tggtgtttac | acgggcctga | gcaccaggaa 240 |
| ccaggagact | tacgagactc | tgaagcatga | gaaaccacca | cagtagcttt | agaatagatg 300 |
| cggtcatatt | cttctttggc | ttctggttct | tccagccctc | atggttggca | tcacatatgc 360 |
| ctgcatgcca | ttaacaccag | ctggccctac | ccctataatg | atcctgtgtc | ctaaattaat 420 |
| atacaccagt | ggttcctcct | ccctgttaaa | gactaatgct | cagatgctgt | ttacggatat 480 |
| ttatattcta | gtctcactct | cttgtcccac | ccttcttctc | ttccccattc | ccaactccag 540 |
| ctaaaatatg | ggaagggaga | accccccaata | aaactgccat | ggactggact | c 591 |

TABLE 5

FcεRI-γ polypeptide sequence (SEQ ID NO: 5)

Met Ile Pro Ala Val Val Leu Leu Leu Leu Leu Val Gln Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Asp Gly Val
        50              55                  60

Tyr Thr Gly Leu Ser Thr Arg Asn Gln Glu Thr Tyr Glu Thr Leu Lys
65              70                  75                  80

His Glu Lys Pro Pro Gln
            85

TABLE 6

TCR-ζ polynucleotide sequence (SEQ ID NO: 6)

| | | | | | |
|---|---|---|---|---|---|
| cttttctcct | aaccgtcccg | gccaccgctg | cctcagcctc | tgcctcccag | cctctttctg 60 |
| agggaaagga | caagatgaag | tggaaggcgc | ttttcaccgc | ggccatcctg | caggcacagt 120 |
| tgccgattac | agaggcacag | agctttggcc | tgctggatcc | caaactctgc | tacctgctgg 180 |
| atgaatcct | cttcatctat | ggtgtcattc | tcactgcctt | gttcctgaga | gtgaagttca 240 |
| gcaggagcgc | agagccccc | gcgtaccagc | agggccagaa | ccagctctat | aacgagctca 300 |
| atctaggacg | aagagaggag | tacgatgttt | tggacaagag | acgtggccgg | gaccctgaga 360 |
| tggggggaaa | gccgagaagg | aagaaccctc | aggaaggcct | gtacaatgaa | ctgcagaaag 420 |

TABLE 6-continued

| TCR-ζ polynucleotide sequence (SEQ ID NO: 6) | |
|---|---|
| ataagatggc ggaggcctac agtgagattg ggatgaaagg cgagcgccgg aggggcaagg | 480 |
| ggcacgatgg cctttaccag ggtctcagta cagccaccaa ggacacctac gacgcccttc | 540 |
| acatgcaggc cctgcccct cgctaacagc caggggattt caccactcaa aggccagacc | 600 |
| tgcagacgcc cagattatga gacacaggat gaagcattta caacccggtt cactcttctc | 660 |
| agccactgaa gtattcccct ttatgtacag gatgctttgg ttatatttag ctccaaacct | 720 |
| tcacacacag actgttgtcc ctgcactctt taagggagtg tactcccagg cttacggcc | 780 |
| ctgccttggg ccctctggtt tgccggtggt gcaggtagac ctgtctcctg gcggttcctc | 840 |
| gttctccctg ggaggcgggc gcactgcctc tcacagctga gttgttgagt ctgttttgta | 900 |
| aagtccccag agaaagcgca gatgctagca catgccctaa tgtctgtatc actctgtgtc | 960 |
| tgagtggctt cactcctgct gtaaatttgg cttctgttgt caccttcacc tcctttcaag | 1020 |
| gtaactgtac tgggccatgt tgtgcctccc tggtgagagg gccgggcaga ggggcagatg | 1080 |
| gaaaggagcc taggccaggt gcaaccaggg agctgcaggg gcatgggaag gtgggcgggc | 1140 |
| aggggagggt cagccagggc ctgcgagggc agcgggagcc tccctgcctc aggcctctgt | 1200 |
| gccgcaccat tgaactgtac catgtgctac aggggccaga agatgaacag actgaccttg | 1260 |
| atgagctgtg cacaaagtgg cataaaaaac agtgtggtta cacagtgtga ataaagtgct | 1320 |
| gcggagcaag aggaggccgt tgattcactt cacgctttca gcgaatgaca aaatcatctt | 1380 |
| tgtgaaggcc tcgcaggaag acgcaacaca tgggacctat aactgcccag cggacagtgg | 1440 |
| caggacagga aaacccgtc aatgtactag gg | 1472 |

TABLE 7

| TCR-ζ polypepticle sequence (SEQ ID NO: 7) |
|---|
| Met Lys Trp Lys Ala Leu Phe Thr Ala Ala Ile Leu Gln Ala Gln Leu<br>1               5                   10                  15 |
| Pro Ile Thr Glu Ala Gln Ser Phe Gly Leu Leu Asp Pro Lys Leu Cys<br>            20                  25                  30 |
| Tyr Leu Leu Asp Gly Ile Leu Phe Ile Tyr Gly Val Ile Leu Thr Ala<br>        35                  40                  45 |
| Leu Phe Leu Arg Val Lys Phe Ser Arg Ser Ala Glu Pro Pro Ala Tyr<br>    50                  55                  60 |
| Gln Gln Gly Gln Asn Gln Leu Tyr Asn Glu Leu Asn Leu Gly Arg Arg<br>65                  70                  75                  80 |
| Glu Glu Tyr Asp Val Leu Asp Lys Arg Arg Gly Arg Asp Pro Glu Met<br>            85                  90                  95 |
| Gly Gly Lys Pro Arg Arg Lys Asn Pro Gln Glu Gly Leu Tyr Asn Glu<br>            100                 105                 110 |
| Leu Gln Lys Asp Lys Met Ala Glu Ala Tyr Ser Glu Ile Gly Met Lys<br>        115                 120                 125 |
| Gly Glu Arg Arg Arg Gly Lys Gly His Asp Gly Leu Tyr Gln Gly Leu<br>    130                 135                 140 |
| Ser Thr Ala Thr Lys Asp Thr Tyr Asp Ala Leu His Met Gln Ala Leu<br>145                 150                 155                 160 |
| Pro Pro Arg |

NK-92 cells are widely used as a model system for the study of NK cell activation, action and inhibition as they stably express a defined suite of known NK cell activating receptors including NKp46, NKp44, 2B4, and NKG2D, but lack CD16, activating KIR, and NKG2C. More importantly, they also lack almost all of the known NK cell inhibitory receptors except low levels of NKG2A/CD94 and ILT2/LIR1. This is a major advantage of the present invention since MHC class I molecules, which are expressed on most cells and serve as ligands for NK cell inhibitory receptors, do not effectively inhibit the activation of NK-92 cells. Furthermore, the present invention restores the CD16 activating receptor to NK-92 cells thereby increasing the range of activating ligands to which these cells respond. Both the activating receptors and any residual inhibitory receptors can be selectively blocked by the treatment of the effector cells with the appropriate monoclonal antibodies or the corresponding $F_{(ab')2}$ fragments, such as 3.43.13 (anti-NKp44), 9E2 (anti-NKp46), 158 (anti-2B4), and 3G8 (anti-CD16). The ability to selectively block individual receptors or groups of receptors in conjunction with target cells that differ in susceptibility to lysis by NK-92 cells (and derivatives thereof) facilitates the study of the many mechanisms involved in NK cell activation and inhibition.

Antibodies (Abs) The invention makes use of Abs and antibody fragments, such as $F_{ab}$ or $(F_{ab'})_2$, that bind immunospecifically to their epitopes.

"Antibody" (Ab) comprises single Abs directed against an epitope, anti-Ab compositions with poly-epitope specificity, single chain anti-Abs, and fragments of Abs. A "monoclonal antibody" is obtained from a population of substantially homogeneous Abs, i.e., the individual Abs comprising the population are identical except for possible naturally-occurring mutations that may be present in minor amounts. Exemplary Abs include polyclonal (pAb), monoclonal (mAb), humanized, bi-specific (bsAb), chimeric and heteroconjugate Abs. Antibodies can be produced by any known method in the art or obtained commercially.

Monovalent Abs

The Abs may be monovalent Abs that consequently do not cross-link with each other. For example, one method involves recombinant expression of immunoglobulin (Ig) light chain and modified heavy chains. Heavy chain truncations generally at any point in the $F_c$ region will prevent heavy chain cross-linking. Alternatively, the relevant cysteine residues are substituted with another amino acid residue or are deleted, preventing cross-linking. In-vitro methods are also suitable for preparing monovalent Abs. Abs can be digested to produce fragments, such as $F_{ab}$ fragments (Harlow and Lane, 1988; Harlow and Lane, 1999).

Humanized and Human Abs

Abs may further comprise humanized or human Abs. Humanized forms of non-human Abs are chimeric Igs, Ig chains or fragments (such as $F_v$, $F_{ab}$, $F_{ab'}$, $F_{(ab')2}$ or other antigen-binding subsequences of Abs) that contain minimal sequence derived from non-human Ig.

Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody (Jones et al., 1986; Riechmann et al., 1988; Verhoeyen et al., 1988). Such "humanized" Abs are chimeric Abs (1989), wherein substantially less than an intact human variable domain has been substituted by the corresponding sequence from a non-human species. In practice, humanized Abs are typically human Abs in which some CDR residues and possibly some Fc residues are substituted by residues from analogous sites in rodent Abs. Humanized Abs include human Igs (recipient antibody) in which residues from a complementary determining region (CDR) of the recipient are replaced by residues from a CDR of a non-human species (donor antibody) such as mouse, rat or rabbit, having the desired specificity, affinity and capacity. In some instances, corresponding non-human residues replace $F_v$ framework residues of the human Ig. Humanized Abs may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region ($F_c$), typically that of a human Ig (Jones et al., 1986; Presta, 1992; Riechmann et al., 1988).

Human Abs can also be produced using various techniques, including phage display libraries (Hoogenboom et al., 1991; Marks et al., 1991) and the preparation of human mAbs (Boerner et al., 1991; Reisfeld and Sell, 1985). Similarly, introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire (1997a; 1997b; 1997c; 1997d; 1997; 1997; Fishwild et al., 1996; 1997; 1997; 2001; 1996; 1997; 1997; 1997; Lonberg and Huszar, 1995; Lonberg et al., 1994; Marks et al., 1992; 1997; 1997; 1997).

Bi-Specific mAbs

Bi-specific Abs are monoclonal, preferably human or humanized, that have binding specificities for at least two different antigens.

Traditionally, the recombinant production of bi-specific Abs is based on the co-expression of two Ig heavy-chain/light-chain pairs, where the two heavy chains have different specificities (Milstein and Cuello, 1983). Because of the random assortment of Ig heavy and light chains, the resulting hybridomas (quadromas) produce a potential mixture of ten different antibody molecules, of which only one has the desired bi-specific structure. The desired antibody can be purified using affinity chromatography or other techniques (Traunecker et al., 1991; 1993).

To manufacture a bi-specific antibody (Suresh et al., 1986), variable domains with the desired antibody-antigen combining sites are fused to Ig constant domain sequences. The fusion is preferably with an Ig heavy-chain constant domain, comprising at least part of the hinge, CH2, and CH3 regions. Preferably, the first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

The interface between a pair of antibody molecules can be engineered to maximize the percentage of heterodimers that are recovered from recombinant cell culture (1996). The preferred interface comprises at least part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This mechanism increases the yield of the heterodimer over unwanted end products such as homodimers.

Bi-specific Abs can be prepared as full length Abs or antibody fragments (e.g. $F_{(ab')2}$ bi-specific Abs). One technique to generate bi-specific Abs exploits chemical linkage. Intact Abs can be proteolytically cleaved to generate $F_{(ab')2}$ fragments (Brennan et al., 1985). Fragments are reduced with a dithiol complexing agent, such as sodium arsenite, to stabilize vicinal dithiols and prevent intermolecular disulfide formation. The generated $F_{ab'}$ fragments are then converted to thionitrobenzoate (TNB) derivatives. One of the $F_{ab'}$-TNB derivatives is then reconverted to the $F_{ab'}$-thiol by reduction with mercaptoethylamine and is mixed with an equimolar amount of the other $F_{ab'}$-TNB derivative to form the bi-specific antibody. The produced bi-specific Abs can be used as agents for the selective immobilization of enzymes.

$F_{ab'}$ fragments may be directly recovered from *E. coli* and chemically coupled to form bi-specific Abs. For example, fully humanized bi-specific $F_{(ab')2}$ Abs can be produced (Shalaby et al., 1992). Each $F_{ab'}$ fragment is separately secreted from *E. coli* and directly coupled chemically in-vitro, forming the bi-specific antibody.

Various techniques for making and isolating bi-specific antibody fragments directly from recombinant cell culture have also been described. For example, leucine zipper motifs can be exploited (Kostelny et al., 1992). Peptides from the Fos and Jun proteins are linked to the $F_{ab'}$ portions of two different Abs by gene fusion. The antibody homodimers are reduced at the hinge region to form monomers and then re-oxidized to form antibody heterodimers. This method can also produce antibody homodimers. The "diabody" technology (Holliger et al., 1993) provides an alternative method to generate bi-specific antibody fragments. The fragments comprise a heavy-chain variable domain ($V_H$) connected to a light-chain variable domain ($V_L$) by a linker that is too short to allow pairing between the two domains on the same chain. The $V_H$ and $V_L$ domains of one fragment are forced to pair with the complementary $V_L$ and $V_H$ domains of another fragment, forming two antigen-binding sites. Another strategy for making bi-specific antibody fragments is the use of single-chain $F_v$ (sF$_v$) dimers (Gruber et al., 1994). Abs with more than two valencies are also contemplated, such as tri-specific Abs (Tutt et al., 1991).

Heteroconjugate Abs

Heteroconjugate Abs, consisting of two covalently joined Abs, have been proposed to target immune system cells to unwanted cells (1987) and for treatment of human immunodeficiency virus (HIV) infection (1991; 1992). Abs prepared in-vitro using synthetic protein chemistry methods, including those involving cross-linking agents, are contemplated. For example, immunotoxins may be constructed using a disulfide exchange reaction or by forming a thioether bond. Examples of suitable reagents include iminothiolate and methyl-4-mercaptobutyrimidate (1987).

Pharmaceutical Compositions for Abs

Abs can be administered in pharmaceutical compositions. Principles and considerations involved in preparing such compositions, as well as guidance in the choice of components, can be found in (de Boer, 1994; Gennaro, 2000; Lee, 1990).

Liposomes can also be used as a delivery vehicle for intracellular introduction. Where antibody fragments are used, the smallest inhibitory fragment that specifically binds to the epitope is preferred. For example, peptide molecules can be designed that bind a preferred epitope based on the variable-region sequences of a useful antibody. Such peptides can be synthesized chemically and/or produced by recombinant DNA technology (Marasco et al., 1993). Formulations may also contain more than one active compound for a particular treatment, preferably those with activities that do not adversely affect each other. The composition can comprise an agent that enhances function, such as a cytotoxic agent, cytokine, chemotherapeutic agent, or growth-inhibitory agent. The composition can also contain cells, such as NK-92 cells.

The active ingredients can also be entrapped in microcapsules prepared by coacervation techniques or by interfacial polymerization; for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macro emulsions.

The formulations to be used for in vivo administration are highly preferred to be sterile. This is readily accomplished by filtration through sterile filtration membranes or any of a number of techniques.

Sustained-release preparations may also be prepared, such as semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (Boswell and Scribner, 1973), copolymers of L-glutamic acid and γ ethyl-L-glutamate, non-degradable ethylene-vinyl acetate, degradable lactic acid-glycolic acid copolymers such as injectable microspheres composed of lactic acid-glycolic acid copolymer, and poly-D-(−)-3-hydroxybutyric acid. While polymers such as ethylene-vinyl acetate and lactic acid-glycolic acid enable release of molecules for over 100 days, certain hydrogels release proteins for shorter time periods and may be preferred.

In a similar manner, the use of multiple antibodies or $F_{(ab')2}$ fragments to specifically block selected activating receptors, permits refinement of the identification of the receptors that are involved in any particular case. In this regard, the presence of NK cell-mediated lysis of a target for which all known activating receptors are blocked is suggestive of the presence of previously unknown activating receptors or ligands. The converse experiment of observing the cytolytic activity of native and transduced NK-92 cells against target cells that have been modified so as to express putative ligands for these receptors can provide additional information and possible confirmation. The cytokine response of the effector cells in these experiments can also provide additional information. Therefore, the invention offers a myriad of options for refining the assay conditions to suit the user's needs, as well as providing a valuable tool for investigations of basic physiological mechanisms of NK cell function.

In addition, the use of antibodies for the therapeutic treatment of disease is a rapidly growing and evolving field. Although the mechanisms involved in the therapeutic effects of antibody treatments are still being elucidated, there is evidence that these effects are mediated by the ad-hoc interaction of the Fc portion of the administered antibody with the corresponding Fc receptors on cytolytic effector cells such as neutrophils, mononuclear phagocytes, transformed cells, T-cells and NK cells. The cytolytic activity of the effector cells is thereby directed against those target cells that display surface antigens that are bound by the antibody. This proposed mechanism is not meant to limit the invention in any way.

The major current thrust of this field involves the use of full-length humanized monoclonal antibodies (thus containing Fc domains) that are directed toward cell surface antigens on tumor cells. For example, substantial clinical benefits have been demonstrated for the treatment of certain breast cancers with the anti-Her2/neu antibody, Herceptin, and the treatment of B cell leukemias with the anti-CD20 antibody, Rituximab. CD16$^+$ effector cells such as native NK cells and the NK-92-CD16 cells and NK-92-CD16γ/ζ cells of this invention bind to the Fc portions of Herceptin or Rituximab antibodies that, in turn, bind via their $F_{(ab)}$ portions to the corresponding cell surface antigen on a cancer cell. This ligation of the cancer cell antigen to CD16 activates the effector cell and directs its cytolytic activity against the cancer cell, thus resulting in its destruction.

Figure 5:
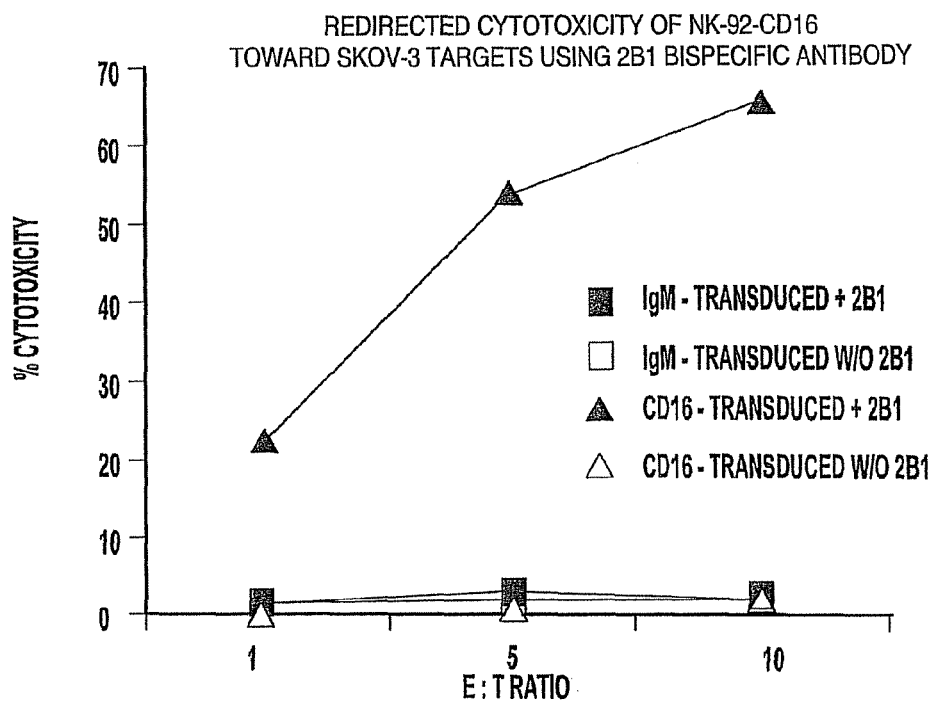
FIG. 5 is a graphical diagram illustrating redirected cytotoxicity of SKOV-3 target cells by NK-92-CD16 cells (triangles), but not mouse IgM-transduced NK-92 (squares), induced by bi-specific 2B1 antibody (filled symbols). 2B1 contains F(ab) domains recognizing both Her2/neu antigen on SKOV-3 cells and CD16 on NK-92-CD16.

Another aspect of development in this area is directed toward the creation of chimeric antibodies that incorporate two or more antigen-binding [$F_{(ab)}$] domains having differing specificities. A chimeric "bi-specific antibody" can, by way of example, incorporate one $F_{(ab)}$ binding domain that specifically binds to a cell surface marker that is uniquely or characteristically expressed on the target tumor or infected cells and a second $F_{(ab)}$ domain that specifically engages activating receptors such as CD16 on NK or other effector cells. Such chimeric antibodies are exemplified by the monoclonal antibody 2B1 (Clark et al., 1997; Weiner et al., 1995a; Weiner et al., 1995b) which incorporates one $F_{(ab)}$ domain that specifically binds to the ErbB2 (HER2/neu) antigen and a second $F_{(ab)}$ domain that specifically binds to CD16. Cells of the ErbB2$^+$ ovarian cancer line SKOV-3 are only slightly susceptible to cytolysis by NK cells or NK-92-CD16 cells. However, SKOV-3 cells become highly susceptible to NK-92-CD16 cell-mediated cytolysis in the presence of 2B1 antibody which ligates the ErbB2 antigen on a SKOV-3 cell to the CD16 activating receptor on a NK-92-CD16 cell. (FIG. 5).

Groner and Moritz (Groner and Moritz, 1997) describe yet another means of using antibodies to direct the activity of an effector cell against a specific target. In this approach, the effector cell is genetically engineered to express a single polypeptide chain consisting of an antigen-specific monovalent $F_{(ab)}$ binding domain that is covalently linked to a signaling domain, such as TCR-ζ (Genbank Accession No. J04132; SEQ ID NO:6).

As illustrated in greater detail below in Example 6, ADCC and redirected cytotoxicity assays can be used to identify antibodies and antibody constructs that are useful as therapeutic agents for the treatment of cancers and infections. NK-92-CD16, NK-92-CD16-γ or NK-92-CD16-ζ cells are used as effector cells in these assays. The target cells and the characteristics of the antibody or antibody construct to be evaluated largely determine whether the ADCC or the redirected cytotoxicity assay format is more appropriate. A target cell that expresses the ligand of interest, but which does not express any Fc receptors is appropriate for the evaluation of antibodies in the ADCC format. This same type of target cell is also suitable for the ADCC evaluation of antibody constructs that include an Fc domain. Conversely, an antibody construct that incorporates separate $F_{(ab)}$ binding domains that are specific for the antigen of interest and for CD16 are most appropriately evaluated via redirected cytotoxicity using target cells that express the antigen of interest, but which do not express CD16. Other such arrangements are likewise possible and can be used in the practice of the present invention. In order to ensure maximum assay dynamic range, it is desirable to select the target cell from among those that are minimally susceptible to lysis by the parental NK-92 cell line. For this reason, the target cell is typically selected to exhibit NK-92 mediated lysis of between 0% and 30%, preferably between 0% and 20%, more preferably between 0% and 10% and most preferably between 0% and 5%. Target cell lines such as SKOV-3 are useful because they exhibit minimal (5%-30%) susceptibility to lysis by NK-92 cells and they constitutively express certain cell surface antigens that are of particular interest as targets for therapeutic antibodies. These cells can also be transduced or transfected to express other antigens of interest and utility.

One significant application of the present invention is in the screening of hybridoma supernates for the presence of ADCC-inducing monoclonal antibodies. The spleen cell fusions employed for the initial generation of monoclonal antibodies result in a heterogeneous population of cells, some of which produce antibodies. Each individual antibody-producing cell in this mixture typically produces a unique antibody that has at least some affinity for the target antigen. The cells in this original heterogeneous mixture are sub-cloned, typically by limiting dilution, to the point where each sub-clone originates from a single parent cell. Each sub-clone is then typically screened to eliminate those that do not secrete immunoglobulins. The remaining sub-clones, which can number in the tens to hundreds, each secrete a unique antibody, a few of which can have specificities, affinities and other characteristics that make them suitable for further evaluation and development as potential therapeutic agents. The ADCC and redirected cytotoxicity assays of Example 6 find utility in the screening of clones to identify those sub-clones that secrete potentially useful antibodies of the IgG isotypes. These same assays can subsequently be used to support the evaluation, characterization and further development of these antibodies.

The present invention consists of NK-92 cell constructs that have been engineered to stably express the fully active, high or low affinity form of the FcγRIII (CD16) receptor. CD16 is naturally present on NK cells, but is not expressed on parental NK-92 cells and/or with any stability by any of the other known NK-like cell lines. The transduced NK-92-CD16, NK-92-CD16-γ and NK-92-CD16-ζ cell lines are, therefore, unique among the presently available NK-like cell lines. Furthermore, NK-92 cells and their genetically engineered derivatives exhibit levels of functional responsiveness in cytotoxicity and cytokine assays that are superior to primary NK cells and most of the other available human NK-like cell lines and appear to be safely tolerated in human subjects. For these reasons, the constructs of the present invention, when used in combination with an antibody that specifically binds to a cell surface marker that is uniquely or characteristically expressed on the intended target cell, provides a substantially higher level of cytolytic activity and specificity toward the target cell type than is provided by parental NK-92 cells or the antibody alone when used in the same manner. Furthermore, unlike native NK cells, the NK-92 cell constructs of this invention express minimal inhibitory receptors, which makes them reactive toward a broad array of tumors. The target cell specificity of these constructs is determined by the co-administered antibody or antibodies, thus permitting these constructs to be used without change for any clinical indication for which a suitable antibody can be prepared. Polyclonal antibodies, cocktails consisting of multiple monoclonal antibodies, and chimeric antibody constructs such as bi-specific antibodies, mini-bodies and TriBi (trimeric, bi-specific) antibodies can be beneficially used in conjunction with this invention.

The present invention can be administered either to animals or to human subjects. When evaluating clinical efficacy, the most beneficial animal models include RAG-deficient/common γ chain-deficient mice (lacking T, B, and NK cells) or SCID mice (lacking T and B cells); these strains are available from The Jackson Laboratory; Bar Harbor, Me. The suppression of the native immune system in such immunocompromised animals facilitates differentiation between responses induced by the treatment and normal immune responses. Furthermore, the cell line derivatives can be used to treat animal subjects, such as bovines, swine, rabbits, alpacas, horses, canines, felines, ferrets, rats, mice, fowl and buffalo, suffering from tumors in combination with tumor-specific antibodies. The therapeutic use of NK-92 cells can be enhanced by preparing subjects who are to receive CD16-transduced NK-92 cells for therapy by infusion the subjects with a low dose of IL-2 for several days prior to administering the NK-92-CD16 cells and targeting antibody, and to continue this infusion for several days afterwards. Alternatively, the CD16-transduced NK-92 cells can be prepared from cells of the NK-92 ml or NK-92ci cell lines that have been engineered to constitutively express IL-2. In either case, concurrent treatment with IL-2 can increase the survival of the administered NK-92 cells.

Since the NK-92 cell line was isolated from a large granular lymphoma subject, the cells have the potential to establish tumors in recipient subjects. Although this tumorigenicity has not been observed in any subjects (human or animal), accepted practice incorporates γ irradiating NK-92 cells prior to administration at doses levels that suppresses NK-92 cell proliferation while substantially maintaining cytotoxicity and cell survival. Gamma irradiation of NK-92 cells at doses of between about 750 and 1000 Grays, e.g., 750, 800, 850, 900 and 950 Grays, is considered to be sufficient for this purpose.

In-vivo treatment of a subject is initiated by administration of the targeting antibody prior to, or concurrently with, the administration of CD16-transduced NK-92 cells. Administration is typically via intravenous or intraperitoneal infusion although direct injection into solid tumors or other such focal lesions can also be used. A split-dose regimen can be preferable, particularly when IL-2 is not being co-administered, in order to maintain a high level of active, transduced NK-92 cells in the subject. In some cases, administering the antibody by infusion and the transduced cells by direct injection can be advantageous. The efficacy of the treatment is generally assessed by lesion reduction/clearance, cytokine profile or other physiological parameters.

The NK-92-CD16, NK-92-CD16/γ and NK-92-CD16/ζ cells of the present invention represent stable and reproducible populations of effector cells that are of particular utility in the in-vitro evaluation of antibodies that are being developed as potential therapeutic agents. These same cell lines are effective components of in-vivo therapies for the treatment of diseases, including cancers and infections. Co-administration of one of these cell lines in conjunction with an antibody that specifically binds to an antigen that is expressed by the tumor or infected cell can potentiate the therapeutic effects of the antibody, thus treating the disease. A similar beneficial effect can be observed in such cases where the cell line is administered as a sole therapy to a subject that has developed endogenous antibodies against a tumor or infection.

In addition, while the Fc receptor CD16 has been exemplified, the present invention is not limited to the expression of FCγRIII-A, and the expression of other Fc receptors for IgG and other antibody types is also within the scope of the invention, including the classes of Fcγ receptors (e.g., FCγRI (CD64), FCγRII (CD32), FCγRIII, and FcRn, Fcα (alpha), Fcε (epsilon), and their various subclasses. Additional NK-92 variant cell lines also fall within the spirit and scope of this invention. NK-92 can, by way of example, be co-transduced with genes leading to the creation of cell lines such as NK-92ci-CD16 and NK-92 ml-CD16 that express both IL-2 and CD16, and that therefore can be used without need for exogenous IL-2. Other benefits and uses of the present invention will be made apparent in the specific examples described below.

Pharmaceutical Compositions

Cells (e.g., modified and unmodified NK-92 cells), polypeptides, and Abs, and derivatives, fragments, analogs and homologs thereof, can be incorporated into pharmaceutical compositions. Such compositions typically comprise the cell, polypeptide, and/or antibody and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (Gennaro, 2000). Preferred examples of such carriers or diluents include, but are not limited to, water, saline, Ringer's solutions, dextrose solution, and 5% human serum albumin. Liposomes and non-aqueous vehicles such as fixed oils may also be used. Supplementary active compounds can also be incorporated into the compositions.

Injectable Formulations

Sterile injectable solutions can be prepared by incorporating the active compound (e.g., an NK-92 cell and/or antibody) in the required amount in an appropriate solvent with one or a combination of ingredients as required, followed by sterilization. Generally, dispersions are prepared by incorporating the active compound into a sterile vehicle that contains a basic dispersion medium, and the other required ingredients as discussed. Sterile powders are used for the preparation of sterile injectable solutions. Methods of preparation include vacuum drying and freeze-drying that yield a powder containing the active ingredient and any desired ingredient from sterile solutions.

EXAMPLES

The following example is for illustrative purposes only and should not be interpreted as limitations of the claimed invention. There are a variety of alternative techniques and procedures available to those of skill in the art which would similarly permit one to successfully perform the intended invention.

Example 1

CD16 Recombinant Retrovirus Preparation

CD16 cDNA X52645.1 encoding the low affinity form of the transmembrane immunoglobulin γ Fc region receptor III-A (FcγRIII-A or CD16) [Phenylalanine-157 (F157), complete sequence: SwissProt P08637 (SEQ ID NO:1)] or a polymorphic variant encoding a higher affinity form of the CD16 receptor [Valine-157 (F157V), complete sequence: SwissProt VAR_008801 (SEQ ID NO:2)] was sub-cloned into the bi-cistronic retroviral expression vector, pBMN-IRES-EGFP (obtained from G. Nolan, Stanford University, Stanford, Calif.) using the BamHI and NotI restriction sites in accordance with standard methods.

The recombinant vector was mixed with 10 µL of PLUS™ Reagent (Invitrogen; Carlsbad, Calif.); diluted to 100 µL with pre-warmed, serum-free Opti-MEM® (Invitrogen; MEM, minimum essential media); further diluted by the addition of 8 µL Lipofectamine™ (Invitrogen) in 100 µL pre-warmed serum-free Opti-MEM®; and incubated at room temperature for 15 minutes. This mixture was then brought to a total volume of 1 mL by the addition of pre-warmed serum-free Opti-MEM®. Phoenix-Amphotropic packaging cells (obtained from G. Nolan, Stanford University, Stanford, Calif.; (Kinsella and Nolan, 1996)) were grown to 70-80% confluence in a 6-well plate and washed with 6 mL of pre-warmed serum-free Opti-MEM® medium (Invitrogen). After removal of the medium, 1 mL of the solution of recombinant vector in Lipofectamine™ PLUS™ Reagent was added to each well, and the cells were incubated for at least three hours at 37° C. under a 7% $CO_2$/balance air atmosphere. Four mL of pre-warmed RPMI medium containing 10% fetal bovine serum (FBS) was added to each well, and the cells incubated overnight at 37° C., under a 7% $CO_2$/balance air atmosphere. The media was then removed; the cells washed with 6 mL pre-warmed serum-free Opti-MEM®; 2 mL serum-free Opti-MEM® added; and the cells incubated at 37° C., under a 7% $CO_2$/balance air atmosphere for an additional 48 hours.

The virus-containing supernate was collected into a 15 mL plastic centrifuge tube; centrifuged at 1300 rpm for 5 minutes to remove cells and cell fragments; and the supernate transferred to another 15 mL plastic centrifuge tube. Immediately before use, 20 µL of PLUS™ Reagent was added to the virus suspension; the mixture incubated at room temperature for 15 minutes; 8 µL Lipofectamine™ added to the mixture; and the mixture incubated for an additional 15 minutes at room temperature.

Example 2

Retroviral Transduction of CD16 into NK-92 Cells

NK-92 cells cultured in A-MEM (Sigma; St. Louis, Mo.) supplemented with 12.5% FBS, 12.5% fetal horse serum (FHS) and 500 IU rhIL-2/mL (Chiron; Emeryville, Calif.) were collected by centrifugation at 1300 rpm for 5 minutes, and the cell pellet was re-suspended in 10 mL serum-free Opti-MEM® medium. An aliquot of cell suspension containing $5 \times 10^4$ cells was sedimented at 1300 rpm for 5 minutes; the cell pellet re-suspended in 2 mL of the retrovirus suspension described in Example 1, and the cells plated into 12-well culture plates. The plates were centrifuged at 1800 rpm for 30 minutes and incubated at 37° C. under an atmosphere of 7% $CO_2$/balance air for 3 hours. This cycle of centrifugation and incubation was then repeated a second time. The cells were diluted with 8 mL of α-MEM, transferred to a T-25 flask, and incubated at 37° C. under a 7% $CO_2$/balance air until the cells were confluent. The transduced cells were collected, re-suspended in serum-free Opti-MEM® medium, and sorted on the basis of their level of EGFP expression using a fluorescence activated cell sorter (FACS), EGFP being co-expressed with, and a surrogate marker for, CD16. Cell-surface expression of CD16 was confirmed by immuno-staining the transduced cells with an anti-CD16 antibody. The transduced cells, which are designated as NK-92-CD16, were passed with fresh IL-2 every 4 days and assayed for cell-surface expression of CD16 before use.

Figure 1B:
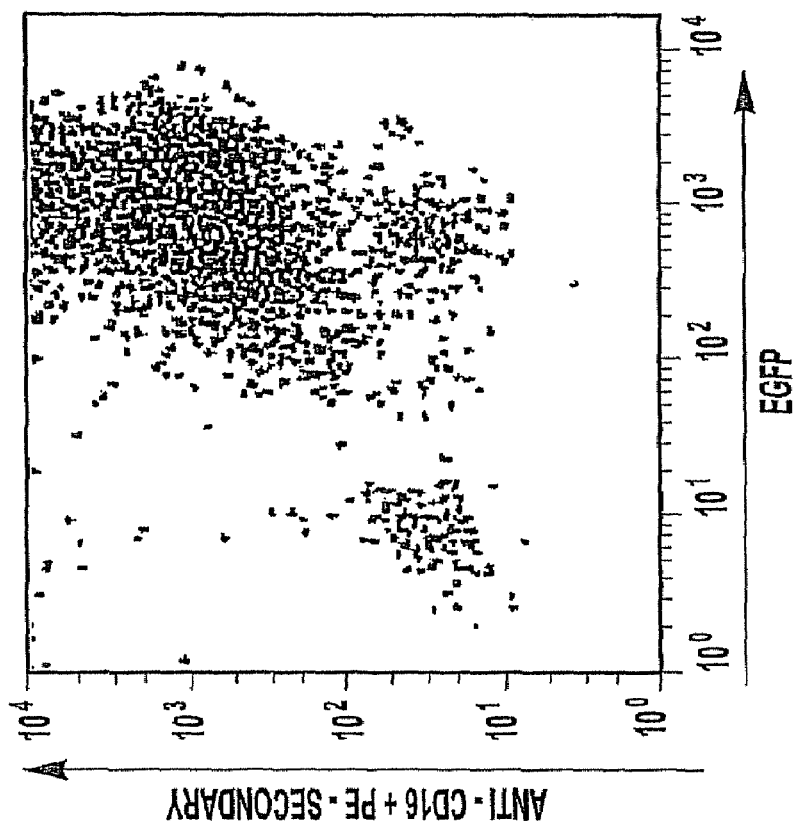

FIGS. 1A and 1B (FIG. 1) are flow cytometer scatter diagrams showing NK-92 cells transduced with CD16 cDNA using the pBMN-IRES-EGFP vector after staining with secondary phycoerythrin (PE)-conjugated anti-mouse IgG antibody alone (FIG. 1A) or anti-CD16 antibody (3G8 (Fleit et al., 1982; Perussia and Trinchieri, 1984); mouse IgG)+PE-anti-mouse IgG (FIG. 1B) and analysis using a FACS (Becton Dickinson; Franklin Lakes, N.J.) flow cytometer. EGFP expression is assessed on the x-axis and surface CD16 expression is on the y-axis. FIG. 1 illustrates that the NK-92-CD16 cell line expresses CD16 on the cell surface when stained with a monoclonal anti-CD16 antibody.

Example 3

NK-92-CD16 Cells Co-Expressing CD16 and an Accessory Signaling Protein FcεRI-γ or TCR-ζ

Recombinant retroviruses incorporating inserted genes for the expression of either accessory signaling proteins, FcεRI-γ (SEQ ID NO:5) or TCR-ζ (SEQ ID NO:7), were prepared by using standard methods to ligate the corresponding cDNA into the pBMN-IRES-EGFP vector and transfecting this construct into the Phoenix-Amphotropic packaging cell line in the presence of Lipofectamine™ Plus as described in Example 1. The resulting γ or ζ recombinant retroviruses were used to transduce NK-92 cells as described in Example 2 with the following further modifications.

NK-92 cells transduced with FcεRI-γ polynucleotide (SEQ ID NO:4) or TCR-ζ (SEQ ID NO:6) were collected, re-suspended in serum-free Opti-MEM® medium and sorted on the basis of their level of the co-expressed EGFP using a FACS, CD16 cDNA was ligated into a version of the pBMN vector lacking the IRES and EGFP sequences, called pBMN-NoGFP (Yusa et al., 2002). The γ- or ζ-transduced NK-92 cells were secondarily co-transduced with CD16-pBMN-NoGFP using the same retroviral transduction method as described in Example 2. The co-transduced cells were suspended in α-MEM, transferred to a T-25 flask, and grown to confluency at 37° C. under a 7% $CO_2$/balance air. After reaching confluency, the co-transduced cells were immuno-stained with an anti-CD16 antibody and sorted by FACS for cell-surface expression of CD16. The selected cells were subcultured with fresh IL-2 every four days and assayed for cell-surface expression of CD16 before use.

In this Example, only one of the two vectors contained the gene for EGFP. This arrangement facilitates the determination of the levels at which both the accessory signaling protein and CD16 are expressed. In this case, the accessory signaling protein was co-expressed with EGFP. Thus EGFP fluorescence is a surrogate indicator for the level of expression of the accessory signaling protein. An anti-CD16 antibody conjugated to a fluorophore having an emission spectrum different from that of EGFP was employed to determine the level of expression of CD16.

Figures 2A, 2B, 2C:
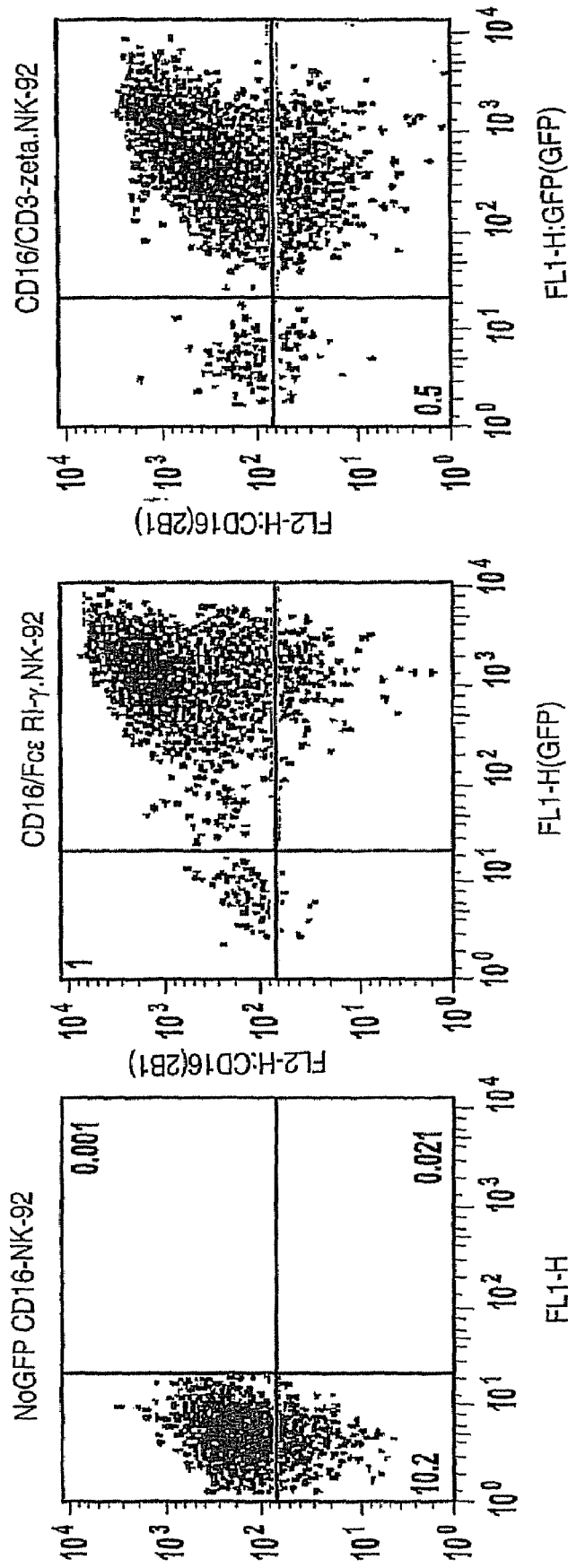
FIG. 2 shows flow cytometer scatter diagrams showing the expression of CD16 by NK-92 cells transduced with CD16 alone (FIG. 2A), and the increase in CD16 expression when NK-92 cells are transduced with CD16 cDNA in combination with FcεRI-γ cDNA (γ; in pBMN-IRES-EGFP vector) (FIG. 2B), or CD3 ζ cDNA (FIG. 2C).

FIG. 2 shows flow cytometer scatter diagrams showing the expression of CD16 by NK-92 cells transduced with CD16 alone (FIG. 2A) and the increase in CD16 expression when NK-92 cells are transduced with CD16 cDNA in combination with FcεRI-γ cDNA (γ; FIG. 2B); or CD3 ζ cDNA (ζ, FIG. 2C). FIG. 2 shows that when CD16 is co-expressed with FcεRI-γ or CD3 ζ in the NK-92 cell line, the cell-surface expression of CD16 is increased over that obtained when NK-92 cells are transduced with CD16 alone.

Example 4

Cytotoxicity Assays

Effector cells (NK-92, NK-92-CD16, NK-92-CD16ζ, NK-92-CD16γ) were washed by suspension in α-MEM (without IL-2) and sedimented at 1300 rpm for 5 minutes. The cell pellet was suspended in α-MEM, cells counted, and aliquots prepared at cell concentrations of $1\times10^5$/mL (effector to target cell ratio (E:T)=1:1), $5\times10^5$/mL (E:T=5:1), $1\times10^6$/mL (E:T=10:1), $2\times10^6$/mL (E:T=20:1) or as appropriate to the determination being performed. The transduced NK-92 cells used in these assays were generally selected for maximal CD16 expression as previously described.

The type of target cell used in these assays was selected on the basis of the requirements of the particular determination being performed. Raji cells (e.g., ATCC Deposit No. CCL-86), which are known to be moderately susceptible (about 50% lysis under these conditions) to lysis by NK-92 cells, were used for most purposes, including verification of the cytotoxicity of the effector cells.

Approximately $2\times10^6$ of the selected target cells were washed by suspension in RPMI medium and sedimentation at 1300 rpm for 5 minutes. After removal of the supernate, 20 μL of FBS and 100 μCi of Na[$^{51}$Cr]chromate was added and the cells incubated at 37° C. for 60-90 minutes with mixing every 30 minutes. The labeled target cells were washed three times by suspension in 10 mL of RPMI medium and sedimentation at 1500 rpm for 5 minutes. The final cell pellet was re-suspended in α-MEM and diluted to a concentration of $1\times10^5$/mL. Target cells for use in redirected cytotoxicity or ADCC assays were further incubated with the appropriate antibody at a final concentration of 0.01-5 μg/mL for 10-15 minutes at room temperature.

One-hundred μL of the selected type of target cells and 100 μL of the appropriate concentration of effector cells were added to each well of a 96 well V-bottom plate. Three to six replicate wells were prepared at each E:T ratio. At least 6 wells were allocated to each of a spontaneous lysis control (effector cells replaced with 100 μL of α-MEM) and total release control (effector cells replaced with 100 μL of 2% t-Octylphenoxypolyethoxyethanol (Triton X-100®) detergent in α-MEM). Desirably, an additional six or more wells are allocated to the use of unmodified NK-92 effector cells that do not express CD16 as a procedural control and internal standard. The plate was then centrifuged at 500 rpm for 3 minutes and incubated for 4 hours at 37° C. in an atmosphere of 7% $CO_2$/balance air. At the end of the incubation period, the plate was centrifuged at 1500 rpm for 8 minutes, and 100 μL of the supernate was collected from each well for counting in a γ counter to measure of $^{51}$Cr release. The percentage of specific target cell lysis was calculated as:

$$\% \text{ specific lysis} = \frac{\left(\begin{array}{c}\text{mean } cpm \text{ experimental release} - \\ \text{mean } cpm \text{ spontaneous lysis}\end{array}\right)}{\left(\begin{array}{c}\text{mean } cpm \text{ total release} - \\ \text{mean } cpm \text{ spontaneous release}\end{array}\right)} \cdot 100$$

Example 5

CD16-Mediated Cell Lysis

Figure 3:
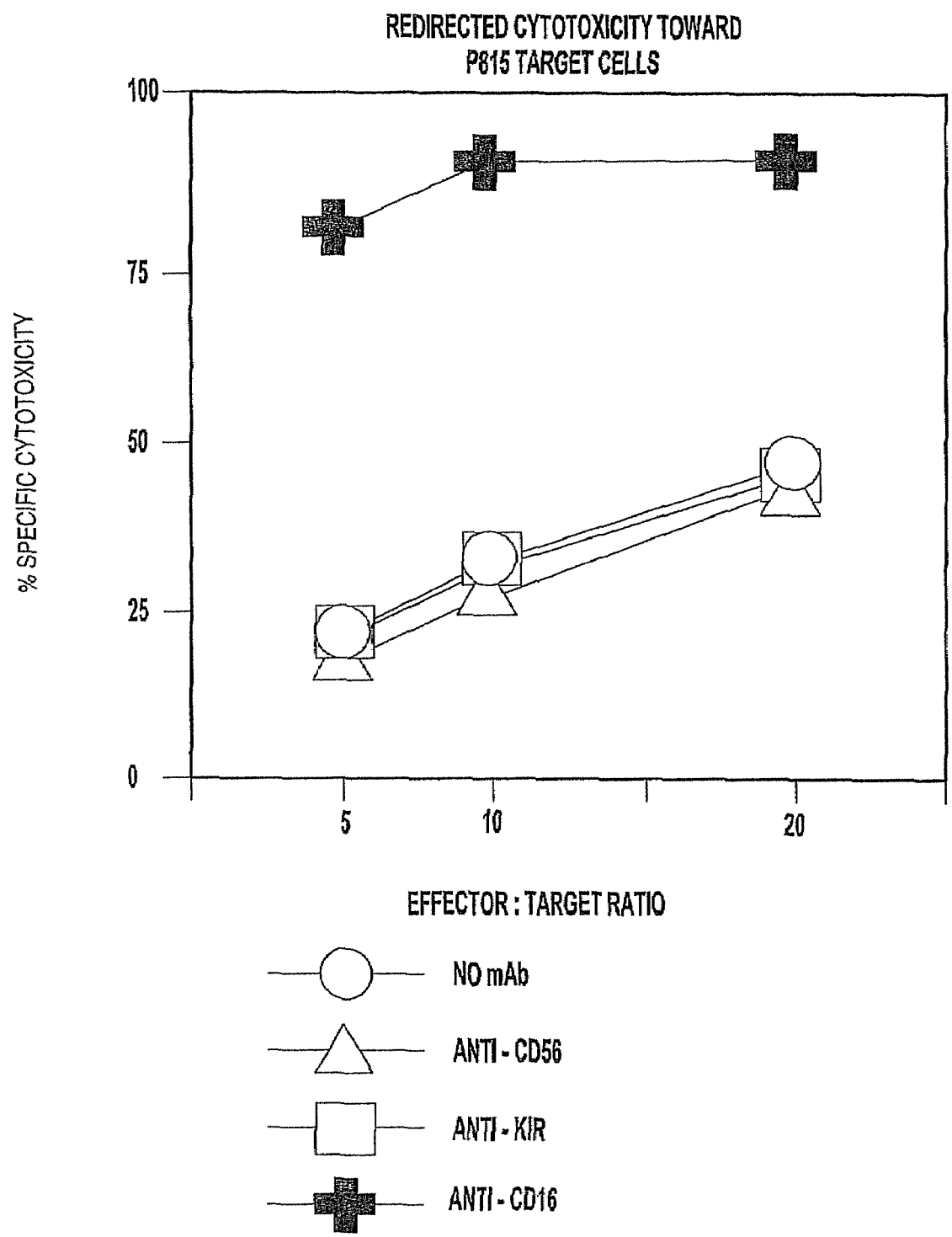
FIG. 3 is a graphical diagram showing redirected cytotoxicity of FcγRII/III+ P815 target cells by NK-92-CD16 cells induced by anti-CD16 antibody (3G8), but not antibodies toward CD56 (B159) or KIR (DX9). Cells were assayed using $^{51}$Cr release from P815 target cells at the indicated effector to target ratios.
Figure 4:
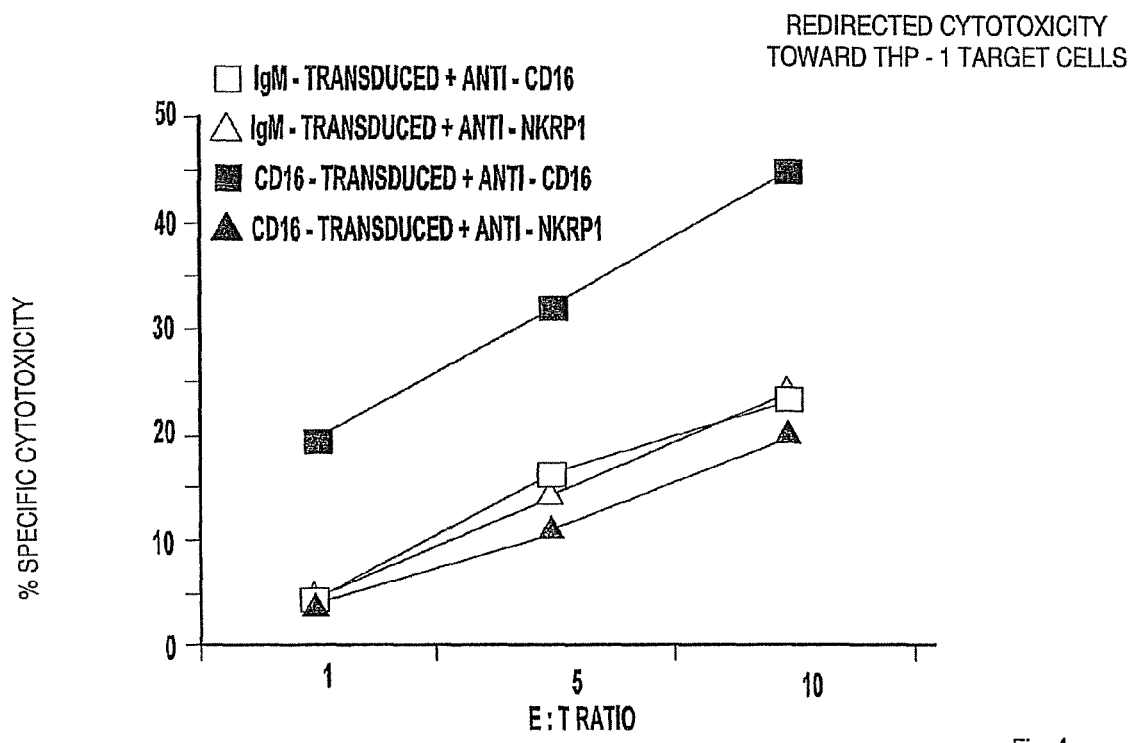
FIG. 4 is a graphical diagram illustrating redirected cytotoxicity of FcγRII/III+ THP-1 target cells by NK-92-CD16 cells (filled symbols) induced by anti-CD16 antibody (3G8; squares), but not anti-NKR-P1 antibody (B199; triangles). Redirected cytotoxicity was not induced by anti-CD16 in NK-92 cells transduced with mouse IgM cDNA (open symbols).
Figure 6:
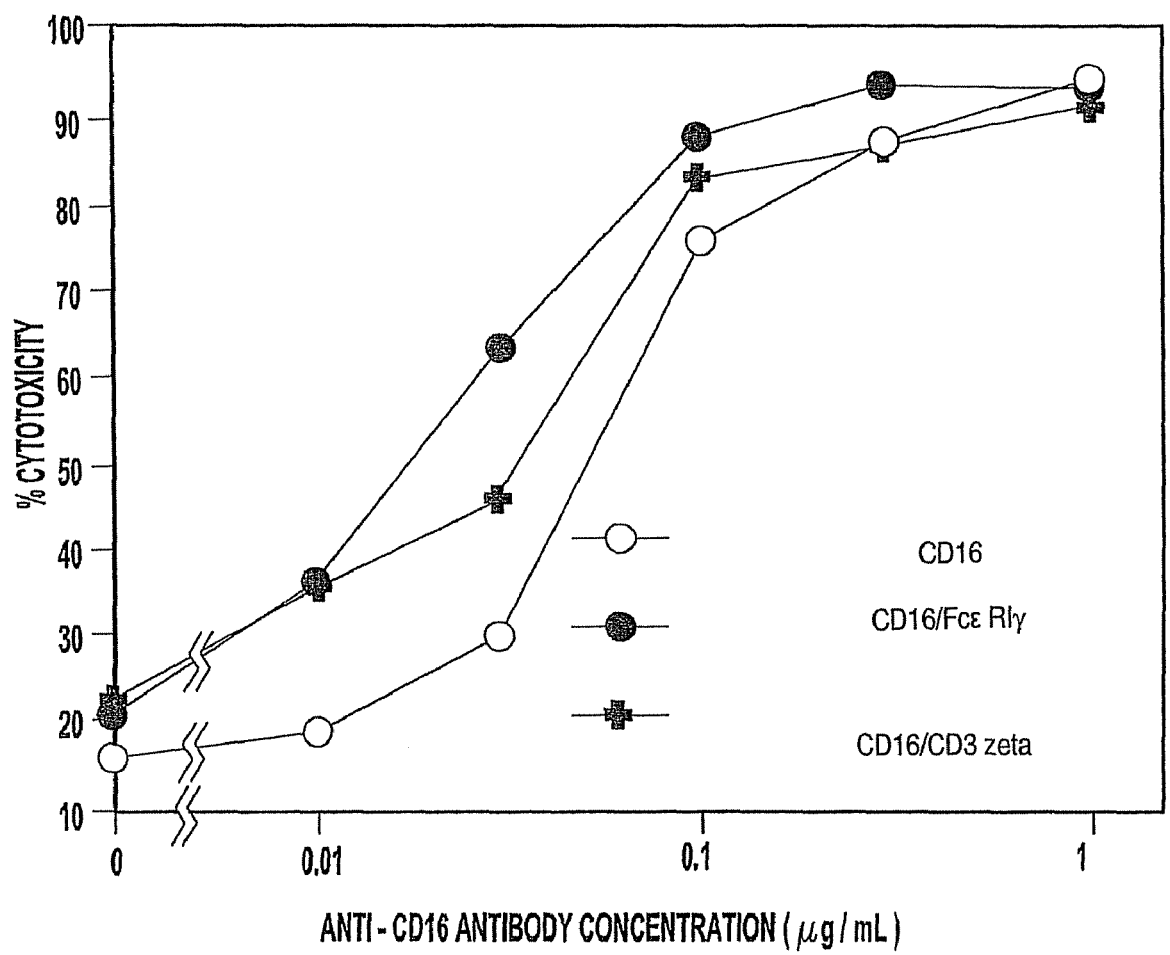
FIG. 6 is a graphical diagram illustrating redirected cytotoxicity of NoGFP NK-92-CD16, NK-92-CD16-γ, and NK-92-CD16-ζ cells against P815 target cells in combination with the indicated concentration of 2B1 chimeric bi-specific monoclonal antibody.

A monoclonal antibody specific for CD16 was used in redirected cytotoxicity assays in those cases where a target cell line that expressed a Fc receptor other than CD16 was available. In particular, the FcgR+ mouse mastocytoma cell line P815 and human FcγR+ myelocytic cell line THP-1 were used as targets in combination with the anti-CD16 monoclonal antibody (mAb) 3G8 (Fleit et al., 1982; Perussia and Trinchieri, 1984) to evaluate NK-92-CD16, NK-92-CD16-γ and NK-92-CD16-ζ cells (FIGS. 3 and 4). In this format, the target cell receptor is thought to bind the Fc portion of the antibody, while the F(ab) portion of the antibody binds to CD16 on the effector cell. Alternatively, redirected cytotoxicity assays can be performed using target cells that express a unique antigen, but which do not express a Fc receptor, in conjunction with a bi-specific antibody construct. In this format, one F(ab) binding domain of the bi-specific antibody specifically binds the target cell antigen while another F(ab) domain specifically binds to CD16. The evaluation of NK-92-CD16, NK-92-CD16-γ or NK-92-CD16-ζ cells in this format was carried out using SKOV-3 as target cells and the chimeric antibody 2B1 as the cross-linking agent. The 2B1 chimeric bi-specific antibody has one binding domain that is specific for HER2/neu and a second binding domain that is specific for CD16 (Clark et al., 1997; Weiner et al., 1995a; Weiner et al., 1995b) (FIG. 5). FIG. 6 illustrates the cytotoxicity of NK-92-CD16, NK-92-CD16-γ and NK-92-CD16-ζ cells against P815 target cells in a redirected cytotoxicity assay using 2B1 chimeric antibody after performing a $^{51}$Cr-release assay for four hours. This Figure shows that at less than saturating antibody concentrations, cytotoxicity is a function of both antibody concentration and the level of expression of CD16 on the NK-92 effector cells.

The following procedure was used in performing both ADCC and redirected cytotoxicity assays, the type of assay being determined by the characteristics of the target cell and selected antibody. The selected target cells were labeled with Na[$^{51}$Cr]chromate as described in Example 4. Aliquots of the $^{51}$[Cr]-labeled target cells were further incubated with the selected antibody at multiple concentrations between 0.01 μg and 5 μg/mL for 15 minutes at room temperature, washed with α-MEM, and adjusted to a concentration of $1\times10^5$ cells/mL before use. One-hundred μL of the selected type of target cells and 100 μL of effector cells at cell concentrations of $1\times10^5$/mL (E:T=1:1), $5\times10^5$/mL (E:T=5:1), $1\times10^6$/mL (E:T=10:1), $2\times10^6$/mL (E:T=20:1) or as appropriate to the determination being performed were added to each well of a 96-well V-bottom plate. Three to six replicate wells were prepared at each E:T ratio to be evaluated. At least 6 wells were allocated to each of a spontaneous lysis control (effector cells replaced with 100 μL of α-MEM) and total release control (effector cells replaced with 100 μL of 2% Triton X-100 detergent in α-MEM). An additional three wells at each E:T ratio were allocated to "non-ADCC" controls in which the target cells were not exposed to the antibody. Desirably, an additional 6 or more wells are allocated to the use of unmodified NK-92 effector cells that do not express CD16 as a procedural control and internal standard. The plate was then centrifuged at 500 rpm for 3 minutes and incubated for 4 hours at 37° C. in an atmosphere of 7% $CO_2$/balance air. At the end of the incubation period, the plate was centrifuged at 1500 rpm for 8 minutes and 100 mL of the supernate was collected from each well for counting in a γ counter as a measure of $^{51}$[Cr] release due to cytotoxicity. The percentage of specific lysis was calculated as described in Example 4.

These assays can also employ NK-92-CD16 cells expressing varying surface levels of CD16 (through cell sorting or via γ or ζ co-transduction), as well as NK-92 transduced with the high affinity polymorphic allele of the CD16 gene (F157V). These variants to the invention provide a broad dynamic range of assay sensitivities. Although this Example is described with reference to monoclonal antibodies and bi-specific antibody constructs, polyclonal antibodies and other

Example 6

Screening and Evaluation of Therapeutic Antibodies

The selected target cells were labeled with Na[$^{51}$Cr]chromate as described in Example 4 and adjusted to a concentration of $1\times10^5$ cells/mL before use. A 100 μL aliquot of labeled target cells was then transferred to each well of the requisite number of 96-well plates. The immunoglobulin concentrations in the hybridoma supernates to be screened were optionally, but preferably, adjusted to a convenient nominal concentration of 1 μg/mL. At least 100 μL aliquots of each hybridoma supernate was added to each of three target cell containing wells; incubated for 15 minutes at room temperature, washed with α-MEM, and re-suspended in 100 μL of α-MEM. The effector cell concentration was adjusted as appropriate to achieve the desired E:T ratio in the assay. For example, if an E:T ratio of 10:1 was desired, the effector cell concentration was adjusted to $1\times10^6$ cells/mL. The assay was initiated by adding 100 μL of effector cells to each well. The plates were then centrifuged at 500 RPM for 3 minutes and incubated for 4 hours at 37° C. in an atmosphere of 7% $CO_2$/balance air. At the end of the incubation period, the plate was centrifuged at 1500 rpm for 8 minutes and 100 μL of the supernate was collected from each well for counting in a γ counter as a measure of $^{51}$[Cr] release due to cytotoxicity. The percentage of specific lysis was calculated as described in Example 4. At least six wells were allocated to each of a spontaneous lysis control (effector cells replaced with 100 μL of α-MEM) and a total release control (effector cells replaced with 100 μL of 2% Triton X-10 detergent in α-MEM) on each plate. An additional six wells in each set of plates was allocated to each of a "no antibody" control (target cells not treated with antibody) and a NK-92 cytolysis control. Specific lysis was reported as the average of three replicate wells after correction for the appropriate controls. Efficacy can be likewise be assessed by the measurement of surrogate indicators such as cytokine release by the NK-92-CD16 cells, the up-regulation of NK cell activation markers such as CD25, CD69 and/or CD95L, activation of transcription factors, such as NF-AT or NF-κB within the NK-92 cells, or the activation of caspases or other markers of apoptosis in the target cells.

In most cases, relatively small numbers (often only one) of antibody constructs were prepared. In such cases, screening was not necessary, and the construct as more conveniently evaluated using a direct assay, such as described in Example 5. Similarly, the relatively few potentially useful antibodies detected during screening were subsequently characterized in more detail using assays such as described in Example 5. Varying concentrations of purified antibodies can be tested to compare efficacies for inducing ADCC. Furthermore, comparative testing of ADCC potential of antibodies on NK-92 cells bearing either low affinity (F157) vs. higher affinity (F157V) forms of CD16 offered a convenient, reproducible assay to address therapeutic efficacies of individual antibodies in the context of both of these known human alleles of CD16. This also circumvented the need for the user to identify specific donors that are homozygous for each of the two alleles for such assays.

Example 7

CD16 Mediated Cytokine Production

Upon activation, NK-92 cells are known to produce and secrete cytokines, including interferon-γ (IFN-γ), tumor necrosis factor (TNF-α and others), interleukins (IL)-5, -10 and -13, granulocyte-macrophage colony-stimulating factor (GM-CSF), nitric oxide and others upon activation. The production of these cytokines can be determined by standard methods including cytokine-specific enzyme-linked immunosorbant assay (ELISA) kits that are available from multiple commercial sources (e.g., BD Pharmingen; San Diego, Calif.). The production of cytokines by NK-92, NK-92-CD16, NK-92-CD16-γ and NK-92-CD16-ζ cells in response to CD16 mediated stimulation can be determined in a manner that is analogous to the ADCC and redirected cytotoxicity assays described in Examples 4 and 5.

Effector cells (NK-92, NK-92-CD16, NK-92-CD16-γ and NK-92-CD16-ζ) were washed by suspension in α-MEM (without IL-2) and sedimentation at 1300 rpm for 5 minutes. The cell pellet was suspended in α-MEM, the cells counted, and aliquots prepared at cell concentrations of $1\times10^5$/mL (E:T=1:1), $5\times10^5$/mL (E:T 5:1), $1\times10^6$/mL (E:T=10:1), $2\times10^6$/mL (E:T=20:1), or as appropriate to the determination being performed.

The type of target cell used in these assays was selected on the basis of the requirements of the particular determination being performed. Raji cells, which are known to be moderately susceptible (about 50% lysis under these conditions) to lysis by NK-92 cells, were used for most purposes, including verification of the cytotoxicity of the effector cells.

One hundred μL of varying concentrations of effector cells were combined with a constant concentration of antibody treated target cells (not labeled with $^{51}$[Cr]) in wells of a 96-well V-bottom plate. Three to six replicate wells were prepared at each E:T ratio to be evaluated. At least 6 wells each were allocated as controls for non-CD16 specific effector cell activation in which the target cells were replaced with 100 mL of α-MEM (spontaneous release) or with 100 μL of 2% Triton X-100 (total release). Additional controls using target cells that have not been antibody treated and target or effector cells that had been treated with F(ab')$_2$ fragments to suppress non-CD16 specific effector cell activation were also included as appropriate. Transduced NK-92 cells expressing different levels or affinities of CD16 could have been used as additional controls in the manner previously described. The plate was centrifuged at 500 rpm for 3 minutes and incubated for 4 hours at 37° C. in an atmosphere of 7% $CO_2$/balance air. At the end of the incubation period, the plate was centrifuged at 1500 rpm for 8 minutes, and aliquots of the supernate were collected from each well to quantify cytokine concentrations, using commercially available cytokine ELISA kits (e.g., BD Pharmingen; San Diego, Calif.). Effector cell cytokine production was generally determined to track effector cell cytotoxicity and could therefore be taken as an alternative indicator of effector cell activation.

Example 8

NK-92 Cell Stimulation by IL-2

Certain cytokines, particularly IL-2, IL-12, IL-15 and IL-18, are known to promote the growth, survival, cytotoxicity and cytokine releasing activities of NK, NK-92, NK-92-CD16, NK-92-CD16-γ and NK-92-CD16-ζ, and other NK-92 variant cells both in-vitro and in-vivo. By way of example, the cells transduced in Examples 2 and 3 proliferated and exhibited stable levels of CD16 expression, cytotoxicity and cytokine response for several months without the need for antibiotic selection when sub-cultured with fresh IL-2-containing medium every 4 days. Conversely, when these same cells were passed without the addition of IL-2, they exhibited cytotoxicity and cytokine production levels that declined with time through the 4-day culture period and returned to higher levels on the first day after fresh IL-2 addition. Furthermore, cells maintained in the absence of IL-2 specifically lysed a narrower range of cell types than did cells maintained in the presence of IL-2. This behavior of transduced NK-92 cells and derivatives closely reflects that of unmodified primary NK cells. For these reasons, it is desirable to assay cells and transduced derivatives at consistent intervals after passage with defined concentrations of IL-2. Similarly, it is desirable to co-administer IL-2 when these cells are being used for in-vivo therapeutic purposes. In those cases where the provision of exogenous IL-2 is inconvenient or otherwise undesirable, the NK-92 ml or NK-92ci cell line that has been engineered to express endogenous IL-2 at levels that promote NK-92 proliferation, survival and activity can also be employed. The NK-92 ml, NK-92ci and other NK-92 derived cell lines can be transduced in the same manners as described for the parent NK-92 cell line in Examples 2 and 3.

From the foregoing, it will be observed that numerous variations and modifications can be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

TABLE Z

Table of Abbreviations

| Abbreviation | Definition |
|---|---|
| ADCC | Antibody-dependent cellular cytotoxicity |
| CD | Cluster of determination |
| CTL | Cytotoxic T-lymphocytes |
| DNA | Deoxyribonucleic acid |
| EGFP | Enhanced green fluorescent protein |
| ELISA | Enzyme-linked immunosorbent assay |
| ErbB2 | Proto-oncogene that encodes a membrane-bound receptor tyrosine kinase of the epithelial growth factor receptor (EGFR) family; also known as HER-2/neu |
| FBS | Fetal bovine serum |
| Fc | Denotes constant region of an antibody |
| FHS | Fetal horse serum |
| GM-CSF | Granulocyte-macrophage colony-stimulating factor |
| IFN | Interferon |
| IL | Interleukin |
| MHC-I | Major histocompatibility complex class I |
| MEM | Minimum essential medium |
| MHC | Major histocompatibility complex |
| NF-AT | nuclear factor of activated T-cells |
| NF-κB | Nuclear factor-κB |
| NK | Natural killer |
| PBL | Peripheral blood lymphocyte |
| RAG | recombinase activating gene |
| RhIL | Recombinant, human interleukin |
| RNA | Ribonucleic acid |
| Rpm | Rotations per minute |
| RPMI | Roswell Park Memorial Institute |
| SCID | Severe combined immunodeficiency |
| TNF | Tumor necrosis factor |
| TriBi | trimeric, bi-specific |

REFERENCES

All references are incorporated herein by reference.

U.S. Pat. No. 4,676,980. 1987. Target specific cross-linked heteroantibodies USA.

U.S. Pat. No. 4,816,567. 1989. Recombinant immunoglobin preparations.

WO 91/00360. 1991. Bispecific reagents for AIDS therapy.

WO 92/20373. 1992. Heteroconjugate antibodies for treatment of HIV infection.

WO 97/33551. 1997a. Compositions and methods for the diagnosis, prevention, and treatment of neoplastic cell growth and proliferation.

U.S. Pat. No. 5,633,425. 1997b. Transgenic non-human animals capable of producing heterologous antibodies USA.

U.S. Pat. No. 5,661,016. 1997c. Transgenic non-human animals capable of producing heterologous antibodies of various isotypes USA.

U.S. Pat. No. 5,625,126. 1997d. Transgenic non-human animals for producing heterologous antibodies USA.

Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. *Nucleic Acids Res.* 25:3389-402.

Austin, C. P., and C. L. Cepko. 1990. Cellular migration patterns in the developing mouse cerebral cortex. *Development.* 110:713-732.

Ausubel, F. M. 2002. Short protocols in molecular biology: a compendium of methods from Current protocols in molecular biology. Wiley, New York. 2 v. (various pagings) pp.

Bodine, D. M., K. T. McDonagh, N. E. Seidel, and A. W. Nienhuis. 1991. Survival and retrovirus infection of murine hematopoietic stem cells in vitro: effects of 5-FU and method of infection. *Exp. Hematol.* 19:206-212.

Boerner, P., R. Lafond, W. Z. Lu, P. Brams, and I. Royston. 1991. Production of antigen-specific human monoclonal antibodies from in vitro-primed human splenocytes. *J Immunol.* 147:86-95.

U.S. Pat. No. 3,773,919. Boswell, G. A., and R. M. Scribner. 1973. Polylactide-drug mixtures USA.

Brennan, M., P. F. Davison, and H. Paulus. 1985. Preparation of bispecific antibodies by chemical recombination of monoclonal immunoglobulin G1 fragments. *Science.* 229:81-3.

Campbell, K. S., S. Yusa, A. Kikuchi-Maki, and T. L. Catina. 2004. NKp44 triggers NK cell activation through DAP12 association that is not influenced by a putative cytoplasmic inhibitory sequence. *J Immunol.* 172:899-906.

Capecchi, M. R. 1980. High efficiency transformation by direct microinjection of DNA into cultured mammalian cells. *Cell.* 22:479.

Carter, P. 1986. Site-directed mutagenesis. *Biochem J.* 237:1-7.

Cepko, C. L., B. E. Roberts, and R. E. Mulligan. 1984. Construction and applications of a highly transmissible murine retrovirus shuttle vector. *Cell.* 37:1053-1062.

Chaney, W. G., D. R. Howard, J. W. Pollard, S. Sallustio, and P. Stanley. 1986. High-frequency transfection of CHO cells using Polybrene. *Somatic Cell Mol. Genet.* 12:237.

Chen, C., and H. Okayama. 1988. Calcium phosphate-mediated gene transfer: A highly efficient system for stably transforming cells with plasmid DNA. *BioTechniques.* 6:632-638.

Clark, J. I., R. K. Alpaugh, M. von Mehren, J. Schultz, J. R. Gralow, M. A. Cheever, D. B. Ring, and L. M. Weiner. 1997. Induction of multiple anti-c-erbB-2 specificities accompanies a classical idiotypic cascade following 2B1 bispecific monoclonal antibody treatment. *Cancer Immunol Immunother.* 44:265-72.

de Boer, A. G. 1994. Drug absorption enhancement: Concepts, possibilities, limitations and trends. Harwood Academic Publishers, Langhorne, Pa.

Elroy-Stein, O., and B. Moss. 1990. Cytoplasmic expression system based on constitutive synthesis of bacteriophage T7 RNA polymerase in mammalian cells. *Proc. Natl. Acad. Sci. USA.* 87:6743-6747.

Escudero, J., and B. Hohn. 1997. Transfer and integration of T-DNA without cell injury in the host plant. *Plant Cell.* 9:2135-2142.

Fekete, D. M., and C. L. Cepko. 1993. Retroviral infection coupled with tissue transplantation limits gene transfer in the chick embryo. *Proc. Natl. Acad. Sci. USA.* 90:2350-2354.

Felgner, P. L., T. R. Gadek, M. Holm, R. Roman, H. W. Chan, M. Wenz, J. P. Northrop, G. M. Ringold, and M. Danielson. 1987. Lipofectin: A highly efficient, lipid-mediated DNA/transfection procedure. *Proc. Natl. Acad. Sci. USA.* 84:7413-7417.

Fieck, A., D. L. Wyborski, and J. M. Short. 1992. Modifications of the *E. coli* Lac repressor for expression in eukaryotic cells: effects of nuclear signal sequences on protein activity and nuclear accumulation. *Nucleic Acids Res.* 20:1785-91.

Fishwild, D. M., S. L. O'Donnell, T. Bengoechea, D. V. Hudson, F. Harding, S. L. Bernhard, D. Jones, R. M. Kay, K. M. Higgins, S. R. Schramm, and N. Lonberg. 1996. High-avidity human IgG kappa monoclonal antibodies from a novel strain of minilocus transgenic mice [see comments]. *Nat Biotechnol.* 14:845-51.

Fleit, H. B., S. D. Wright, and J. C. Unkeless. 1982. Human neutrophil Fc gamma receptor distribution and structure. *Proc Natl Acad Sci USA.* 79:3275-9.

Fujita, T., H. Shubiya, T. Ohashi, K. Yamanishi, and T. Taniguchi. 1986. Regulation of human interleukin-2 gene: Functional DNA sequences in the 5' flanking region for the gene expression in activated T lymphocytes. *Cell.* 46:401-407.

Gennaro, A. R. 2000. Remington: The science and practice of pharmacy. Lippincott, Williams & Wilkins, Philadelphia, Pa.

Gerstmayer, B., B. Groner, W. Wels, and B. S. Schnierle. 1999. Stable expression of the ecotropic retrovirus receptor in amphotropic packaging cells facilitates the transfer of recombinant vectors and enhances the yield of retroviral particles. *J Virol Methods.* 81:71-5.

Gong, J. H., G. Maki, and H. G. Klingemann. 1994. Characterization of a human cell line (NK-92) with phenotypical and functional characteristics of activated natural killer cells. *Leukemia.* 8:652-8.

Graham, F. L., and A. J. van der Eb. 1973. A new technique for the assay of infectivity of human adenovirus 5 DNA. *Virology.* 52:456.

EP Patent No. EP0758394. Groner, B., and D. Moritz. 1997. Bifunctional protein, preparation and use European Patent Office.

Gruber, M., B. A. Schodin, E. R. Wilson, and D. M. Kranz. 1994. Efficient tumor cell lysis mediated by a bispecific single chain antibody expressed in *Escherichia coli*. *J Immunol.* 152:5368-74.

Harlow, E., and D. Lane. 1988. Antibodies: A laboratory manual. Cold Spring Harbor Laboratory Press, Cold Spring Harbor. 726 pp.

Harlow, E., and D. Lane. 1999. Using antibodies: A laboratory manual. Cold Spring Harbor Laboratory Press, Cold Spring Harbor, N.Y.

Holliger, P., T. Prospero, and G. Winter. 1993. "Diabodies": small bivalent and bispecific antibody fragments. *Proc Natl Acad Sci USA.* 90:6444-8.

Hoogenboom, H. R., A. D. Griffiths, K. S. Johnson, D. J. Chiswell, P. Hudson, and G. Winter. 1991. Multi-subunit proteins on the surface of filamentous phage: methodologies for displaying antibody (Fab) heavy and light chains. *Nucleic Acids Res.* 19:4133-7.

Houdebine, L. M. 1997. Transgenic animals: Generation and use. Harwood Academic Press, Amsterdam, The Netherlands. 576 pp.

Huang, J. Y., and D. L. Brutlag. 2001. The EMOTIF database. *Nucleic Acids Res.* 29:202-4.

Ishiura, M., S. Hirose, T. Uchida, Y. Hamada, Y. Suzuki, and Y. Okada. 1982. Phage particle-mediated gene transfer to cultured mammalian cells. *Molecular and Cellular Biology.* 2:607-616.

Jones, P. T., P. H. Dear, J. Foote, M. S. Neuberger, and G. Winter. 1986. Replacing the complementarity-determining regions in a human antibody with those from a mouse. *Nature.* 321:522-5.

Kaufman, R. J. 1990. Vectors used for expression in mammalian cells. *Methods Enzymol.* 185:487-511.

Kawai, S., and M. Nishizawa. 1984. New procedure for DNA transfection with polycation and dimethyl sulfoxide. *Mol. Cell. Biol.* 4:1172.

Kikuchi-Maki, A., S. Yusa, T. L. Catina, and K. S. Campbell. 2003. KIR2DL4 is an IL-2-regulated NK cell receptor that exhibits limited expression in humans but triggers strong IFN-gamma production. *J Immunol.* 171:3415-25.

Kinsella, T. M., and G. P. Nolan. 1996. Episomal vectors rapidly and stably produce high-titer recombinant retrovirus. *Hum Gene Ther.* 7:1405-13.

20020068044 (publication). Klingemann, H. G. 2002. Natural killer cell lines and methods of use USA.

Koehne, G., H. F. Guo, D. Trivedi, R. Y. Williams, R. J. O'Reilly, and N.-K. V. Cheung. 2003. Redirection NK-cell cytolytic activity to solid tumors using chemieric scFv receptor gene-modified adoptive immunotherapy. In Proc. Am. Soc. Clin. Oncol. Vol. 22. 175 (Abstract 703).

Koene, H. R., M. Kleijer, J. Algra, D. Roos, A. E. von dem Borne, and M. de Haas. 1997. Fc gammaRIIIa-158V/F polymorphism influences the binding of IgG by natural killer cell Fc gammaRIIIa, independently of the Fc gammaRIIIa-48L/R/H phenotype. *Blood.* 90:1109-14.

Komatsu, F., and M. Kajiwara. 1998. Relation of natural killer cell line NK-92-mediated cytolysis (NK-92-lysis) with the surface markers of major histocompatibility complex class I antigens, adhesion molecules, and Fas of target cells. *Oncol Res.* 10:483-9.

Kostelny, S. A., M. S. Cole, and J. Y. Tso. 1992. Formation of a bispecific antibody by the use of leucine zippers. *J Immunol.* 148:1547-53.

Lam, K. S. 1997. Application of combinatorial library methods in cancer research and drug discovery. *Anticancer Drug Design.* 12:145-167.

Lee, V. H. L. 1990. Peptide and protein drug delivery. Marcel Dekker, New York, N.Y.

Lemischka, I. R., D. H. Raulet, and R. C. Mulligan. 1986. Developmental potential and dynamic behavior of hematopoietic stem cells. *Cell.* 45:917-927.

Linder, M. W., R. A. Prough, and R. Valdes. 1997. Pharmacogenetics: a laboratory tool for optimizing therapeutic efficiency. *Clin Chem.* 43:254-66.

Lonberg, N., and D. Huszar. 1995. Human antibodies from transgenic mice. *Int Rev Immunol.* 13:65-93.

Lonberg, N., L. D. Taylor, F. A. Harding, M. Trounstine, K. M. Higgins, S. R. Schramm, C. C. Kuo, R. Mashayekh, K. Wymore, J. G. McCabe, and et al. 1994. Antigen-specific human antibodies from mice comprising four distinct genetic modifications [see comments]. *Nature.* 368:856-9.

Lopata, M. A., D. W. Cleveland, and B. Sollner-Webb. 1984. High-level expression of a chloramphenicol acetyltransferase gene by DEAEdextran-mediated DNA transfection coupled with a dimethylsulfoxide or glycerol shock treatment. *Nucleic Acids Research.* 12:5707.

Maki, G., H. G. Klingemann, J. A. Martinson, and Y. K. Tam. 2001. Factors regulating the cytotoxic activity of the human natural killer cell line, NK-92. *J Hematother Stem Cell Res.* 10:369-83.

Marasco, W. A., W. A. Haseltine, and S. Y. Chen. 1993. Design, intracellular expression, and activity of a human anti-human immunodeficiency virus type 1 gp120 single-chain antibody. *Proc Natl Acad Sci USA.* 90:7889-93.

Marks, J. D., A. D. Griffiths, M. Malmqvist, T. P. Clackson, J. M. Bye, and G. Winter. 1992. By-passing immunization: building high affinity human antibodies by chain shuffling. *Biotechnology (N Y).* 10:779-83.

Marks, J. D., H. R. Hoogenboom, T. P. Bonnert, J. McCafferty, A. D. Griffiths, and G. Winter. 1991. By-passing immunization. Human antibodies from V-gene libraries displayed on phage. *J Mol Biol.* 222:581-97.

Miller, A. D., and C. Buttimore. 1986. Redesign of retrovirus packaging cell lines to avoid recombination leading to helper virus production. *Mol. Cell biol.* 6:2895-2902.

Milstein, C., and A. C. Cuello. 1983. Hybrid hybridomas and their use in immunohistochemistry. *Nature.* 305:537-40.

Nagashima, S., R. Mailliard, Y. Kashii, T. E. Reichert, R. B. Herberman, P. Robbins, and T. L. Whiteside. 1998. Stable transduction of the interleukin-2 gene into human natural killer cell lines and their phenotypic and functional characterization in vitro and in vivo. *Blood.* 91:3850-61.

Neumann, E., M. Schaefer-Ridder, Y. Wang, and P. H. Hofschneider. 1982. Gene transfer into mouse lyoma cells by electroporation in high electric fields. *EMBO J.* 1:841-845.

U.S. Pat. No. 5,830,725. Nolan, G. P., and T. Kinsella. 1998. Rapid, stable high-titre production of recombing retrovirus USA.

Pear, W., G. Nolan, M. Scott, and D. Baltimore. 1993. Production of high-titer helper-free retroviruses by transient transfection. *Proc. Natl. Acad. Sci. USA.* 90:8392-8396.

Pende, D., S. Parolini, A. Pessino, S. Sivori, R. Augugliaro, L. Morelli, E. Marcenaro, L. Accame, A. Malaspina, R. Biassoni, C. Bottino, L. Moretta, and A. Moretta. 1999. Identification and molecular characterization of NKp30, a novel triggering receptor involved in natural cytotoxicity mediated by human natural killer cells. *J Exp Med.* 190:1505-16.

Perussia, B., and G. Trinchieri. 1984. Antibody 3G8, specific for the human neutrophil Fc receptor, reacts with natural killer cells. *J Immunol.* 132:1410-5.

Pessino, A., S. Sivori, C. Bottino, A. Malaspina, L. Morelli, L. Moretta, R. Biassoni, and A. Moretta. 1998. Molecular cloning of NKp46: a novel member of the immunoglobulin superfamily involved in triggering of natural cytotoxicity. *J Exp Med.* 188:953-60.

Potter, H. 1988. Electroporation in biology: Methods, applications, and instrumentation. *Analytical Biochemistry.* 174:361-373.

Potter, H., L. Weir, and P. Leder. 1984. Enhancer-dependent expression of human kappa immunoglobulin genes introduced into mouse pre-B lymphocytes by electroporation. *Proc. Natl. Acad. Sci. USA.* 81:7161-7165.

Presta, L. G. 1992. Antibody engineering. *Curr Opin Biotechnol.* 3:394-8.

Rassoulzadegan, M., B. Binetruy, and F. Cuzin. 1982. High frequency of gene transfer after fusion between bacteria and eukaryotic cells. *Nature.* 295:257.

Reid, G. S., S. Bharya, H. G. Klingemann, and K. R. Schultz. 2002. Differential killing of pre-B acute lymphoblastic leukaemia cells by activated NK cells and the NK-92 ci cell line. *Clin Exp Immunol.* 129:265-71.

Reisfeld, R. A., and S. Sell. 1985. Monoclonal antibodies and cancer therapy: Proceedings of the Roche-UCLA symposium held in Park City, Utah, Jan. 26-Feb. 2, 1985. Alan R. Liss, New York. 609 pp.

Riechmann, L., M. Clark, H. Waldmann, and G. Winter. 1988. Reshaping human antibodies for therapy. *Nature.* 332:323-7.

Rose, J. K., L. Buonocore, and M. Whitt. 1991. A new cationic liposome reagent mediating nearly quantitative transfection of animal cells. *BioTechniques.* 10:520-525.

Sambrook, J., and D. W. Russell. 2001. Molecular cloning: a laboratory manual. Cold Spring Harbor Laboratory Press, Cold Spring Harbor, N.Y.

Sandri-Goldin, R. M., A. L. Goldin, J. C. Glorioso, and M. Levine. 1981. High-frequency transfer of cloned herpes simplex virus type I sequences to mammalian cells by protoplast fusion. *Mol. Cell. Biol.* 1:7453-752.

Schaffner, W. 1980. Direct transfer of cloned genes from bacteria to mammalian cells. *Proc. Natl. Acad. Sci. USA.* 77:2163.

Selden, R. F., K. Burke-Howie, M. E. Rowe, H. M. Goodman, and D. D. Morre. 1986. Human growth hormone as a reporter gene in regulation studies employing transient gene expression. *Molecular and Cellular Biology.* 6:3173-3179.

Shalaby, M. R., H. M. Shepard, L. Presta, M. L. Rodrigues, P. C. Beverley, M. Feldmann, and P. Carter. 1992. Development of humanized bispecific antibodies reactive with cytotoxic lymphocytes and tumor cells overexpressing the HER2 protooncogene. *J Exp Med.* 175:217-25.

Suresh, M. R., A. C. Cuello, and C. Milstein. 1986. Bispecific monoclonal antibodies from hybrid hybridomas. *Methods Enzymol.* 121:210-28.

Tam, Y. K., G. Maki, B. Miyagawa, B. Hennemann, T. Tonn, and H. G. Klingemann. 1999. Characterization of genetically altered, interleukin 2-independent natural killer cell lines suitable for adoptive cellular immunotherapy. *Hum Gene Ther.* 10:1359-73.

Touraev, A., and et. al. 1997. Plant male germ line transformation. *Plant J.* 12:949-956.

Traunecker, A., F. Oliveri, and K. Karjalainen. 1991. Myeloma based expression system for production of large mammalian proteins. *Trends Biotechnol.* 9:109-13.

Trick, H. N., and et. al. 1997. Recent advances in soybean transformation. *Plant Tissue Cult. Biotechnol.* 3:9-26.

Turner, D. L., E. Y. Snyder, and C. L. Cepko. 1990. Lineage-independent determination of cell type in the embryonic mouse retina. *Neuron.* 4:833-845.

Tutt, A., G. T. Stevenson, and M. J. Glennie. 1991. Trispecific F(ab')3 derivatives that use cooperative signaling via the TCR/CD3 complex and CD2 to activate and redirect resting cytotoxic T cells. *J Immunol.* 147:60-9.

Uherek, C., B. Groner, and W. Wels. 2001. Chimeric antigen receptors for the retargeting of cytotoxic effector cells. *J Hematother Stem Cell Res.* 10:523-34.

Uherek, C., T. Tonn, B. Uherek, S. Becker, B. Schnierle, H. G. Klingemann, and W. Wels. 2002. Retargeting of natural killer-cell cytolytic activity to ErbB2-expressing cancer cells results in efficient and selective tumor cell destruction. *Blood.* 100:1265-73.

Verhoeyen, M., C. Milstein, and G. Winter. 1988. Reshaping human antibodies: grafting an antilysozyme activity. *Science.* 239:1534-6.

Vitale, M., C. Bottino, S. Sivori, L. Sanseverino, R. Castriconi, E. Marcenaro, R. Augugliaro, L. Moretta, and A. Moretta. 1998. NKp44, a novel triggering surface molecule specifically expressed by activated natural killer cells, is involved in non-major histocompatibility complex-restricted tumor cell lysis. *J Exp Med.* 187:2065-72.

Weiner, L. M., J. I. Clark, M. Davey, W. S. Li, I. Garcia de Palazzo, D. B. Ring, and R. K. Alpaugh. 1995a. Phase I trial of 2B1, a bispecific monoclonal antibody targeting c-erbB-2 and Fc gamma RIII. *Cancer Res.* 55:4586-93.

Weiner, L. M., J. I. Clark, D. B. Ring, and R. K. Alpaugh. 1995b. Clinical development of 2B1, a bispecific murine monoclonal antibody targeting c-erbB-2 and Fc gamma RIII. *J Hematother.* 4:453-6.

Weiner, L. M., M. Holmes, A. Richeson, A. Godwin, G. P. Adams, S. T. Hsieh-Ma, D. B. Ring, and R. K. Alpaugh. 1993. Binding and cytotoxicity characteristics of the bispecific murine monoclonal antibody 2B1. *J Immunol.* 151:2877-86.

Wells, J. A., M. Vasser, and D. B. Powers. 1985. Cassette mutagenesis: an efficient method for generation of multiple mutations at defined sites. *Gene.* 34:315-23.

Whitt, M. A., L. Buonocore, J. K. Rose, V. Ciccarone, and G. Gebeyehu. 1990. TransfectACE reagent promotes transient transfection frequencies greater than 90%. *Focus.* 13:8-12.

Wigler, M., A. Pellicer, S. Silversttein, and R. Axel. 1978. Biochemical transfer of single-copy eucaryotic genes using total cellular DNA as donor. *Cell.* 14:725.

Wilmut, I., A. E. Schnieke, J. McWhir, A. J. Kind, and K. H. Campbell. 1997. Viable offspring derived from fetal and adult mammalian cells. *Nature.* 385:810-3.

Wong, T. K., and E. Neumann. 1982. Electric field mediated gene transfer. *Biochemical and Biophysical Research Communications.* 107:584-587.

Wyborski, D. L., L. C. DuCoeur, and J. M. Short. 1996. Parameters affecting the use of the lac repressor system in eukaryotic cells and transgenic animals. *Environ Mol Mutagen.* 28:447-58.

Wyborski, D. L., and J. M. Short. 1991. Analysis of inducers of the *E. coli* lac repressor system in mammalian cells and whole animals. *Nucleic Acids Res.* 19:4647-53.

Yan, Y., P. Steinherz, H. G. Klingemann, D. Dennig, B. H. Childs, J. McGuirk, and R. J. O'Reilly. 1998. Antileukemia activity of a natural killer cell line against human leukemias. *Clin Cancer Res.* 4:2859-68.

Yusa, S., and K. S. Campbell. 2003. Src homology region 2-containing protein tyrosine phosphatase-2 (SHP-2) can play a direct role in the inhibitory function of killer cell Ig-like receptors in human NK cells. *J Immunol.* 170:4539-47.

Yusa, S., T. L. Catina, and K. S. Campbell. 2002. SHP-1- and phosphotyrosine-independent inhibitory signaling by a killer cell Ig-like receptor cytoplasmic domain in human NK cells. *J Immunol.* 168:5047-57.

Yusa, S., T. L. Catina, and K. S. Campbell. 2004. KIR2DL5 can inhibit human NK cell activation via recruitment of Src homology region 2-containing protein tyrosine phosphatase-2 (SHP-2). *J Immunol.* 172:7385-92.

Zoller, M. J., and M. Smith. 1987. Oligonucleotide-directed mutagenesis: a simple method using two oligonucleotide primers and a single-stranded DNA template. *Methods Enzymol.* 154:329-50.

---

The invention claimed is:

1. A modified NK-92 cell available from American Type Culture Collection as Deposit No. PTA-8836.

2. A modified NK-92 cell available from American Type Culture Collection as Deposit No. PTA-6967.

* * * * *